US008735324B2

(12) United States Patent
Jentzer et al.

(10) Patent No.: US 8,735,324 B2
(45) Date of Patent: May 27, 2014

(54) ESTERAMIDE SOLVENTS/COALESCING AGENTS IN PHYTOSANITARY, CLEANING, DEGREASING, STRIPPING, LUBRICATING, COATING, AND PIGMENT/INK COMPOSITIONS

(75) Inventors: Olivier Jentzer, Vourles (FR); Massimo Guglieri, Paris (FR)

(73) Assignee: Rhodia Operations, Aubervilliers (FR)

( * ) Notice: Subject to any disclaimer, the term of this patent is extended or adjusted under 35 U.S.C. 154(b) by 455 days.

(21) Appl. No.: 12/864,119

(22) PCT Filed: Jan. 23, 2009

(86) PCT No.: PCT/EP2009/050780
§ 371 (c)(1),
(2), (4) Date: Mar. 24, 2011

(87) PCT Pub. No.: WO2009/092795
PCT Pub. Date: Jul. 30, 2009

(65) Prior Publication Data
US 2011/0166025 A1    Jul. 7, 2011

(30) Foreign Application Priority Data

Jan. 25, 2008 (FR) ..................... 08 00393
Sep. 18, 2008 (FR) ..................... 08 05133

(51) Int. Cl.
*A01N 25/00* (2006.01)
*C07C 229/46* (2006.01)
*C04B 16/00* (2006.01)
*C10M 129/68* (2006.01)
*C09K 3/00* (2006.01)
*C05F 11/00* (2006.01)
*A01P 13/00* (2006.01)

(52) U.S. Cl.
USPC ......... 504/358; 71/27; 106/31.3; 106/287.25; 106/505; 252/364; 508/500; 514/563; 560/170

(58) Field of Classification Search
USPC ......... 71/27; 106/31.3, 287.25, 505; 252/364; 504/358; 508/500; 514/563; 560/170
See application file for complete search history.

(56) References Cited

U.S. PATENT DOCUMENTS 4,020,099 A     4/1977  Kuceski
4,588,833 A *   5/1986  Kadelka et al. ............... 560/145

FOREIGN PATENT DOCUMENTS

| DE | 1040234 | | 10/1958 |
| EP | 14933361 | B1 | 1/2005 |
| JP | 02169554 | * | 6/1990 |

OTHER PUBLICATIONS

JACS, 1979, 101(5), 1316-1318.*
English translation of the Written Opinion mailed Sep. 14, 2010.

* cited by examiner

*Primary Examiner* — Shailendra Kumar
(74) *Attorney, Agent, or Firm* — Dentons US LLP

(57) ABSTRACT

Esteramide compounds are useful solvents/coalescing agents for a variety of phytosanitary, cleaning, degreasing, stripping, lubricating, coating and pigment/ink compositions.

29 Claims, No Drawings

ESTERAMIDE SOLVENTS/COALESCING AGENTS IN PHYTOSANITARY, CLEANING, DEGREASING, STRIPPING, LUBRICATING, COATING, AND PIGMENT/INK COMPOSITIONS

CROSS-REFERENCE TO PRIOR APPLICATIONS

This application is a national stage of PCT/EP 2009/050780, filed Jan. 23, 2009 and designating the United States (published in the French language on Jul. 30, 2009, as WO 2009/092795 A1; the title and abstract were also published in English) and claims priority under 35 U.S.C. §119 of FR 0800393, filed Jan. 25, 2008, FR 0805133, filed Sep. 18, 2008, each hereby expressly incorporated by reference in its entirety and each assigned to the assignee hereof.

One subject of the present invention is the use, as solvents, of compounds of esteramide type. Another subject of the invention are particularly practical processes for preparing esteramides. Another subject of the invention are novel esteramides, which may in particular be used as solvents, for example in phytosanitary formulations.

Industry uses many chemical compounds as solvents, for example for preparing chemicals and materials, for formulating chemical compounds, or for treating surfaces. For example, solvents are used for the formulation of phytosanitary active agents especially in the form of emulsifiable concentrates (ECs) intended to be diluted in water by the farmer before being applied to a field.

Industry is looking for novel compounds that make it possible to vary or optimize the products and processes in which solvents, especially polar solvents, are to be used. Industry needs, in particular, compounds of moderate cost, that have advantageous usage properties. Industry also needs compounds that have a toxicological and/or ecological profile that is perceived as favourable, in particular a low volatility (low VOCs), good biodegradability, low toxicity and/or a low hazard level.

The use of dialkylamides as solvents is known. These are products of formula R—CONMe$_2$ where R is a hydrocarbon-based group, such as an alkyl group, typically a C$_6$-C$_{30}$ group. Such products are sold, in particular, under the name Genagen® by Clariant. These solvents find applications, in particular, in the phytosanitary field.

Also known as solvents are the diesters of dicarboxylic acids, especially the diesters obtained by esterification of a mixture of adipic acid, glutaric acid and succinic acid. Such products are sold, in particular, under the names Rhodiasolv® RPDE and Rhodiasolv® DIB by Rhodia.

Document U.S. Pat. No. 4,588,833 (the priority applications of which have been published as DE 3339386 and DE 3420112) describes a process for preparing esteramides by reaction, at high temperature, catalysed by cobalt, of an unsaturated amide with an alcohol and carbon monoxide. It is furthermore mentioned that the compounds prepared may be used as stabilizers for polymers. The esteramides prepared are the following:

| Example 1 | Mixture of A and B |
| --- | --- |
| | A: PhOOC—CH(CH$_3$)—CH$_2$—CONEt$_2$ |
| | B: PhOOC—CH$_2$—CH$_2$—CH$_2$—CONEt$_2$ |
| Examples 2-6 | C: EtOOC—CH(CH$_3$)—CH$_2$—CONEt$_2$ |
| Example 7 | D: MeOOC—CH(CH$_3$)—CH$_2$—CONEt$_2$ |
| Examples 8-9 | E: Me—CH(OMe)—OOC—CH(CH$_3$)—CH$_2$—CONEt$_2$ |
| Example 10 | F: Cyclohexyl-OOC—CH(CH$_3$)—CH$_2$—CONEt$_2$ |
| Example 11 | G: Ph—CH$_2$OOC—CH(CH$_3$)—CH$_2$—CONEt$_2$ (by virtue of the reactants) |
| Example 12 | H: p-cresyl-OOC—CH(CH$_3$)—CH$_2$—CONEt$_2$ |
| Examples 18-20 | I: EtOOC—CHEt—CH$_2$—CONEt$_2$ + J: EtOOC—CH(CH$_3$)—CH$_2$—CH$_2$—CONEt$_2$ + K: EtOOC—CH$_2$—CH$_2$—CH$_2$—CH$_2$—CONEt$_2$ |

The compound of formula L: MeOOC—CHEt-CH$_2$—CONMe$_2$ was identified by the CAS Registry Number® 368212-04-8, by reference to document WO 01/79167 relating to a remote field, the relevance of which is uncertain.

The compound of formula M: MeOOC—CH$_2$—CH(CH$_3$)—CH$_2$—CONH(n-butyl) was identified by the CAS Registry Number® 538326-02-2, by reference to a document relating to enzymatic reactions.

The compound of formula N: MeOOC—CH$_2$—CH(CH$_3$)—CH$_2$—CONMe$_2$ was identified by the CAS Registry Number® 70367-41-8, by reference to a document relating to the use of lithium enolates.

Document U.S. Pat. No. 3,417,114 describes, in example 9, the compound denoted by DMGME, of formula O: MeOOC—CH$_2$—CH$_2$—CH$_2$—CONMe$_2$. This compound is prepared by reaction of dimethyl glutarate with dimethylamine, then isolation of the DMGME by distillation from the complex mixture obtained (it is in fact a by-product). DMGME is said to have a melting point of 7.5° C.

Document U.S. Pat. No. 3,288,794 comprises similar teachings.

Document U.S. Pat. No. 4,020,099 mentions products such as DMGME and furthermore mentions the crystallization of diphenyl terephthalate in solvents. DMGME is not however used.

The compound of formula P: MeOOC—CH$_2$—CH$_2$—CONMe$_2$ was identified by the CAS Registry Number® 30891-34-0, by reference to documents relating to remote fields, the relevance of which is uncertain.

Document DE 1040234 describes the following compounds and their use as plasticizers:

C$_4$H$_9$—OOC—CH$_2$—CH$_2$—CONEt$_2$

C$_6$H$_{13}$—OOC—(CH$_2$)$_8$—CON(C$_3$H$_7$)$_2$

C$_8$H$_{17}$—OOC—(CH$_2$)$_8$—CON(C$_4$H$_9$)$_2$

C$_8$H$_{17}$—OOC—(CH$_2$)$_8$—CON(C$_8$H$_{17}$)$_2$

There remains a need, as explained above, for novel solvents, in particular in phytosanitary formulations, and for novel compounds. There is also a need for more efficient processes for preparing esteramides.

The invention meets at least one of the needs mentioned above by proposing the use, as a solvent or coalescing agent, of an esteramide compound of formula (I) below:

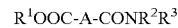

R$^1$OOC-A-CONR$^2$R$^3$  (I)

where:

R$^1$ is a group chosen from saturated or unsaturated, linear or branched, optionally cyclic, optionally aromatic hydrocarbon-based groups comprising an average number of carbon atoms ranging from 1 to 36;

R$^2$ and R$^3$, which are identical or different, are groups chosen from saturated or unsaturated, linear or branched, optionally cyclic, optionally aromatic, optionally substituted hydrocarbon-based groups comprising an average number of carbon atoms ranging from 1 to 36, it being possible for R$^2$ and R$^3$ to optionally together form a ring, that is optionally substituted and/or that optionally comprises a heteroatom; and A is a linear or branched divalent alkyl group comprising an average number of carbon atoms ranging from 2 to 12, preferably from 2 to 4.

It is mentioned that $R^1$ may be a group different from a menthyl group.

Another subject of the invention is a process for solvation, co-solvation, plasticization, coalescence and/or inhibition of crystallization by addition of the compound of the invention. Another subject of the invention are formulations comprising the compound of the invention. The formulations may especially be phytosanitary formulations.

According to one particular embodiment of the invention, if A is linear, then the esteramide compound is used in a phytosanitary composition, a cleaning, degreasing or stripping composition. According to another particular embodiment, if A is branched, then the esteramide compound is used in a phytosanitary composition, a cleaning, degreasing or stripping composition.

According to one particular embodiment of the invention, if $R^2$ and $R^3$ are ethyl groups, then the esteramide compound is used in a phytosanitary composition, a cleaning, degreasing or stripping composition.

Another subject of the invention is at least one process for preparing the esteramide compound.

Another subject of the invention are novel esteramide compounds which may be particularly suitable for the uses mentioned above. In this respect the invention also relates to an esteramide compound of formula (I) below:

$$R^1OOC\text{-}A\text{-}CONR^2R^3 \quad (I)$$

where:

$R^1$ is a group chosen from saturated or unsaturated, linear or branched, optionally cyclic, optionally aromatic hydrocarbon-based groups comprising an average number of carbon atoms ranging from 1 to 36;

$R^2$ and $R^3$, which are identical or different, are groups chosen from saturated or unsaturated, linear or branched, optionally cyclic, optionally aromatic, optionally substituted hydrocarbon-based groups comprising an average number of carbon atoms ranging from 1 to 36, it being possible for $R^2$ and $R^3$ to optionally together form a ring, that is optionally substituted and/or that optionally comprises a heteroatom; and A is a linear or branched divalent alkyl group comprising an average number of carbon atoms ranging from 2 to 12, preferably from 2 to 4, except for the following compounds or mixtures:

MeOOC—CHEt-CH$_2$—CONMe$_2$;

MeOOC—CH$_2$—CH(CH$_3$)—CH$_2$—CONMe$_2$;

MeOOC—CH$_2$—CH$_2$—CH$_2$—CONMe$_2$;

MeOOC—CH$_2$—CH$_2$—CONMe$_2$;

mixture of PhOOC—CH(CH$_3$)—CH$_2$—CONEt$_2$ and PhOOC—CH$_2$—CH$_2$—CH$_2$—CONEt$_2$;

EtOOC—CH(CH$_3$)—CH$_2$—CONEt$_2$;

MeOOC—CH(CH$_3$)—CH$_2$—CONEt$_2$;

Me-CH(OMe)-OOC—CH(CH$_3$)—CH$_2$—CONEt$_2$;

Cyclohexyl-OOC—CH(CH$_3$)—CH$_2$—CONEt$_2$;

Ph-CH$_2$OOC—CH(CH$_3$)—CH$_2$—CONEt$_2$;

p-cresyl-OOC—CH(CH$_3$)—CH$_2$—CONEt$_2$;

mixture of EtOOC—CHEt-CH$_2$—CONEt$_2$, EtOOC—CH(CH$_3$)—CH$_2$—CH$_2$—CONEt$_2$ and EtOOC—CH$_2$—CH$_2$—CH$_2$—CH$_2$—CONEt$_2$;

MeOOC—CH$_2$—CH(CH$_3$)—CH$_2$—CONH(n-butyl), if the latter, individually, are not used as a mixture with other compounds corresponding to formula (I).

It is also possible to exclude the following compounds or mixtures:

C$_4$H$_9$—OOC—CH$_2$—CH$_2$—CONEt$_2$

C$_6$H$_{13}$—OOC—(CH$_2$)$_8$—CON(C$_3$H$_7$)$_2$

C$_8$H$_{17}$—OOC—(CH$_2$)$_8$—CON(C$_4$H$_9$)$_2$

C$_8$H$_{17}$—OOC—(CH$_2$)$_8$—CON(C$_8$H$_{17}$)$_2$ if the latter, individually, are not used as a mixture with other compounds corresponding to formula (I).

DEFINITIONS

In the present application the term "solvent" is understood in a broad sense, in particular covering the functions of co-solvent, crystallization inhibitor and stripping agent. The term solvent may especially denote a product that is liquid at the usage temperature, preferably having a melting point less than or equal to 20° C., preferably 5° C., preferably 0° C., which may contribute to rendering a solid substance liquid, or to preventing or retarding the solidification or the crystallization of material in a liquid medium.

In the present application the expression "compound of the invention" denotes any compound corresponding to the general formula (I). It is mentioned that the term "compound" also covers mixtures of several molecules corresponding to the general formula (I). It may therefore be a molecule of formula (I) or a mixture of several molecules of formula (I). Such a compound may especially be a "novel compound of the invention" excluding the following compounds or mixtures (the latter possibly being denoted as "former compounds of the invention"):

MeOOC—CHEt-CH$_2$—CONMe$_2$;

MeOOC—CH$_2$—CH(CH$_3$)—CH$_2$—CONMe$_2$;

MeOOC—CH$_2$—CH$_2$—CH$_2$—CONMe$_2$;

MeOOC—CH$_2$—CH$_2$—CONMe$_2$;

mixture of PhOOC—CH(CH$_3$)—CH$_2$—CONEt$_2$ and PhOOC—CH$_2$—CH$_2$—CH$_2$—CONEt$_2$;

EtOOC—CH(CH$_3$)—CH$_2$—CONEt$_2$;

MeOOC—CH(CH$_3$)—CH$_2$—CONEt$_2$;

Me-CH(OMe)-OOC—CH(CH$_3$)—CH$_2$—CONEt$_2$;

Cyclohexyl-OOC—CH(CH$_3$)—CH$_2$—CONEt$_2$;

Ph-CH$_2$OOC—CH(CH$_3$)—CH$_2$—CONEt$_2$;

p-cresyl-OOC—CH(CH$_3$)—CH$_2$—CONEt$_2$;

mixture of EtOOC—CHEt-CH$_2$—CONEt$_2$, EtOOC—CH(CH$_3$)—CH$_2$—CH$_2$—CONEt$_2$ and EtOOC—CH$_2$—CH$_2$—CH$_2$—CH$_2$—CONEt$_2$; and MeOOC—CH$_2$—CH(CH$_3$)—CH$_2$—CONH(n-butyl).

It is also possible to exclude from the field of the "novel compounds of the invention" the following compounds or mixtures:

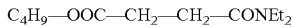

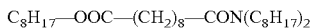

In the present application, the expression "composition of matter", is understood to mean a more or less complex composition comprising several chemical compounds. It may typically be an unpurified or moderately purified reaction product. The compound of the invention will especially be able to be isolated and/or sold and/or used in the form of a composition of matter comprising it. If the compound of the invention is a mixture of several compounds of formula (I) then it is also a composition of matter. The compound of the invention, in the form of a pure molecule or in the form of a mixture corresponding to formula (I), may be included in a composition of matter.

In the composition of matter, the compound of the invention may represent at least 10% by weight. Preferably, it is the main compound of the composition of matter. The expression "main compound" is understood in the present application to mean the compound having the highest content, even if its content is less than 50% by weight (for example, in a mixture of 40% of A, 30% of B and 30% of C, the product A is the main compound). More preferably still, the compound of the invention represents at least 50% by weight of the composition of matter, for example from 70 to 95% by weight, and even from 75 to 90% by weight. As indicated above, the composition of matter may be a reaction product.

Compound of the Invention

The compound of the invention is a compound of general formula (I) given above.

The $R^1$, $R^2$ and $R^3$ groups, which are identical or different, may especially be groups chosen from $C_1$-$C_{12}$ alkyl, aryl, alkaryl or arylalkyl groups or the phenyl group. The $R^2$ and $R^3$ groups may optionally be substituted, in particular by hydroxyl groups.

The $R^1$ group may especially be chosen from methyl, ethyl, propyl, isopropyl, n-butyl, isobutyl, n-pentyl, isopentyl, isoamyl, n-hexyl, cyclohexyl, 2-ethylbutyl, n-octyl, isooctyl, 2-ethylhexyl, tridecyl groups.

The $R^2$ and $R^3$ groups, which are identical or different, may especially be chosen from methyl, ethyl, propyl (n-propyl), isopropyl, n-butyl, isobutyl, n-pentyl, amyl, isoamyl, hexyl, cyclohexyl or hydroxyethyl groups. The $R^2$ and $R^3$ groups may also be such that they form, together with the nitrogen atom, a morpholine, piperazine or piperidine group. According to particular embodiments, $R^2$=$R^3$=methyl, or $R^2$=$R^3$=ethyl, or $R^2$=$R^3$=hydroxyethyl.

According to one particular embodiment, if A comprises a linear group of formula —$CH_2$—$CH_2$— and/or of formula —$CH_2$—$CH_2$—$CH_2$—$CH_2$— and/or of formula —$(CH_2)_8$— then it is a mixture of A groups. According to one particular embodiment, if A is linear, then it is a mixture of A groups, for example a mixture of two or three —$CH_2$—$CH_2$— (ethylene); —$CH_2$—$CH_2$—$CH_2$— (n-propylene); and —$CH_2$—$CH_2$—$CH_2$—$CH_2$— (n-butylene) groups.

According to a first particular embodiment of the invention, the A group is a divalent linear alkyl group chosen from the groups of the following formulae: —$CH_2$—$CH_2$— (ethylene); —$CH_2$—$CH_2$—$CH_2$— (n-propylene); —$CH_2$—$CH_2$—$CH_2$—$CH_2$— (n-butylene), and mixtures thereof.

According to one particular variant in this first embodiment, the compound of the invention is chosen from the following compounds:

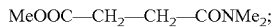

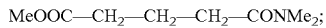

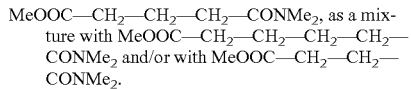

According to a second particular embodiment of the invention, the A group is a divalent branched alkylene group having one of the following formulae (IIa), (IIb), (IIc), (IIIa) and (IIIb), or a mixture of at least two groups chosen from the groups of formulae (IIa), (IIb) and (IIc) or from the groups of formulae (IIIa) and (IIIb), or a mixture of at least two groups, one chosen from the groups of formulae (IIa), (IIb) and (IIc) and the others chosen from the groups of formulae (IIIa) and (IIIb):

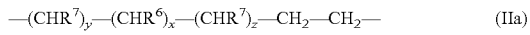 (IIa)

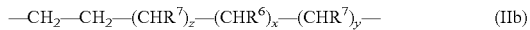 (IIb)

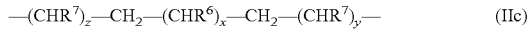 (IIc)

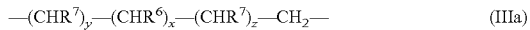 (IIIa)

 (IIIb)

where:
x is an integer greater than 0;
y is an average integer greater than or equal to 0;
z is an average integer greater than or equal to 0;
$R^6$, which is identical or different, is a $C_1$-$C_6$, preferably $C_1$-$C_4$, alkyl group; and
$R^7$, which is identical or different, is a hydrogen atom or a $C_1$-$C_6$, preferably $C_1$-$C_4$, alkyl group.

In this second particular embodiment, the A group is preferably a group such that y=z=0.

Preferably, in the formula (IIa) and/or in the formula (IIb): –x=1; y=z=0; $R^6$=methyl.

Preferably, in the formula (IIIa) and/or in the formula (IIIb): –x=1; y=z=0; $R^6$=ethyl.

According to one particular variant in the second particular embodiment, the compound of the invention is chosen from the following compounds, and mixtures thereof:

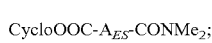

CycloOOC-A$_{MG}$-CONEt$_2$;

CycloOOC-A$_{ES}$-CONEt$_2$;

BuOOC-A$_{MG}$-CONEt$_2$;

BuOOC-A$_{ES}$-CONEt$_2$;

BuOOC-A$_{MG}$-CONMe$_2$;

BuOOC-A$_{ES}$-CONMe$_2$;

EtBuOOC-A$_{MG}$-CONMe$_2$;

EtBuOOC-A$_{ES}$-CONMe$_2$;

n-HeOOC-A$_{MG}$-CONMe$_2$;

n-HeOOC-A$_{ES}$-CONMe$_2$;

where

A$_{MG}$ represents an MG$_a$ group of formula —CH(CH$_3$)—CH$_2$—CH$_2$—, or MG$_b$ group of formula —CH$_2$—CH$_2$—CH(CH$_3$)— or a mixture of MG$_a$ and MG$_b$ groups;

A$_{ES}$ represents an ES$_a$ group of formula —CH(C$_2$H$_5$)—CH$_2$—, or ES$_b$ group of formula —CH$_2$—CH(C$_2$H$_5$)— or a mixture of ES$_a$ and ES$_b$ groups;

Pe represents a pentyl group, preferably an isopentyl or isoamyl group;

Cyclo represents a cyclohexyl group;

Eh represents a 2-ethylhexyl group;

Bu represents a butyl group, preferably an n-butyl or tert-butyl group;

EtBu represents an ethylbutyl group; and n-He represents an n-hexyl group.

It is mentioned that according to one particular variant of one or the other of the particular embodiments of the invention, the compound of the invention is a compound different from the following compounds:

MeOOC—CHEt-CH$_2$—CONMe$_2$;

MeOOC—CH$_2$—CH(CH$_3$)—CH$_2$—CONMe$_2$;

MeOOC—CH$_2$—CH$_2$—CH$_2$—CONMe$_2$; and

MeOOC—CH$_2$—CH$_2$—CONMe$_2$;

if the latter are not used as a mixture with other compounds corresponding to formula (I).

It is mentioned that according to one even more particular variant of one or the other of the particular embodiments of the invention, the compound of the invention is a novel compound of the invention, different from the following compounds or mixtures, if the latter, individually, are not used as a mixture with other compounds corresponding to formula (I):

MeOOC—CHEt-CH$_2$—CONMe$_2$;

MeOOC—CH$_2$—CH(CH$_3$)—CH$_2$—CONMe$_2$;

MeOOC—CH$_2$—CH$_2$—CH$_2$—CONMe$_2$;

MeOOC—CH$_2$—CH$_2$—CONMe$_2$;

mixture of PhOOC—CH(CH$_3$)—CH$_2$—CONEt$_2$ and PhOOC—CH$_2$—CH$_2$—CH$_2$—CONEt$_2$;

EtOOC—CH(CH$_3$)—CH$_2$—CONEt$_2$;

MeOOC—CH(CH$_3$)—CH$_2$—CONEt$_2$;

Me-CH(OMe)-OOC—CH(CH$_3$)—CH$_2$—CONEt$_2$;

Cyclohexyl-OOC—CH(CH$_3$)—CH$_2$—CONEt$_2$;

Ph-CH$_2$OOC—CH(CH$_3$)—CH$_2$—CONEt$_2$;

p-cresyl-OOC—CH(CH$_3$)—CH$_2$—CONEt$_2$;

mixture of EtOOC—CHEt-CH$_2$—CONEt$_2$, EtOOC—CH(CH$_3$)—CH$_2$—CH$_2$—CONEt$_2$ and EtOOC—CH$_2$—CH$_2$—CH$_2$—CH$_2$—CONEt$_2$; and MeOOC—CH$_2$—CH(CH$_3$)—CH$_2$—CONH(n-butyl).

It is mentioned that according to one even more particular variant of one or the other of the particular embodiments of the invention, the compound of the invention is a novel compound of the invention, different from the following compounds or mixtures, if the latter, individually, are not used as a mixture with other compounds corresponding to formula (I):

C$_4$H$_9$—OOC—CH$_2$—CH$_2$—CONEt$_2$

C$_6$H$_{13}$—OOC—(CH$_2$)$_8$—CON(C$_3$H$_7$)$_2$

C$_8$H$_{17}$—OOC—(CH$_2$)$_8$—CON(C$_4$H$_9$)$_2$

C$_8$H$_{17}$—OOC—(CH$_2$)$_8$—CON(C$_8$H$_{17}$)$_2$.

It is mentioned that it is possible to use the following compounds as a mixture with other compounds corresponding to formula (I):

MeOOC—CHEt-CH$_2$—CONMe$_2$;

MeOOC—CH$_2$—CH(CH$_3$)—CH$_2$—CONMe$_2$;

MeOOC—CH$_2$—CH$_2$—CH$_2$—CONMe$_2$;

MeOOC—CH$_2$—CH$_2$—CONMe$_2$;

mixture of PhOOC—CH(CH$_3$)—CH$_2$—CONEt$_2$ and PhOOC—CH$_2$—CH$_2$—CH$_2$—CONEt$_2$;

EtOOC—CH(CH$_3$)—CH$_2$—CONEt$_2$;

MeOOC—CH(CH$_3$)—CH$_2$—CONEt$_2$;

Me-CH(OMe)-OOC—CH(CH$_3$)—CH$_2$—CONEt$_2$;

Cyclohexyl-OOC—CH(CH$_3$)—CH$_2$—CONEt$_2$;

Ph-CH$_2$OOC—CH(CH$_3$)—CH$_2$—CONEt$_2$;

p-cresyl-OOC—CH(CH$_3$)—CH$_2$—CONEt$_2$;

mixture of EtOOC—CHEt-CH$_2$—CONEt$_2$, EtOOC—CH(CH$_3$)—CH$_2$—CH$_2$—CONEt$_2$ and EtOOC—CH$_2$—CH$_2$—CH$_2$—CH$_2$—CONEt$_2$;

MeOOC—CH$_2$—CH(CH$_3$)—CH$_2$—CONH(n-butyl);

C$_4$H$_9$—OOC—CH$_2$—CH$_2$—CONEt$_2$;

C$_6$H$_{13}$—OOC—(CH$_2$)$_8$—CON(C$_3$H$_7$)$_2$;

C$_8$H$_{17}$—OOC—(CH$_2$)$_8$—CON(C$_4$H$_9$)$_2$; and

C$_8$H$_{17}$—OCC—(CH$_2$)$_8$—CON(C$_8$H$_{17}$)$_2$.

It is mentioned that according to one still more particular variant of one or the other of the particular embodiments of the invention, the following compounds or mixtures are not used:

MeOOC—CHEt-CH$_2$—CONMe$_2$;

MeOOC—CH$_2$—CH(CH$_3$)—CH$_2$—CONMe$_2$;

MeOOC—CH$_2$—CH$_2$—CH$_2$—CONMe$_2$;

MeOOC—CH$_2$—CH$_2$—CONMe$_2$;

mixture of PhOOC—CH(CH$_3$)—CH$_2$—CONEt$_2$ and PhOOC—CH$_2$—CH$_2$—CH$_2$—CONEt$_2$;

EtOOC—CH(CH$_3$)—CH$_2$—CONEt$_2$;

MeOOC—CH(CH$_3$)—CH$_2$—CONEt$_2$;

Me-CH(OMe)-OOC—CH(CH$_3$)—CH$_2$—CONEt$_2$;

Cyclohexyl-OOC—CH(CH$_3$)—CH$_2$—CONEt$_2$;

Ph-CH$_2$OOC—CH(CH$_3$)—CH$_2$—CONEt$_2$;

p-cresyl-OOC—CH(CH$_3$)—CH$_2$—CONEt$_2$;

mixture of EtOOC—CHEt-CH$_2$—CONEt$_2$, EtOOC—CH(CH$_3$)—CH$_2$—CH$_2$—CONEt$_2$ and EtOOC—CH$_2$—CH$_2$—CH$_2$—CH$_2$—CONEt$_2$; and MeOOC—CH$_2$—CH(CH$_3$)—CH$_2$—CONH(n-butyl).

It is mentioned that according to one still more particular variant of one or the other of the particular embodiments of the invention, the following compounds or mixtures are not used:

C$_4$H$_9$—OOC—CH$_2$—CH$_2$—CONEt$_2$;

C$_6$H$_{13}$—OOC—(CH$_2$)$_8$—CON(C$_3$H$_7$)$_2$;

C$_8$H$_{17}$—OOC—(CH$_2$)$_8$—CON(C$_4$H$_9$)$_2$;

C$_8$H$_{17}$—OOC—(CH$_2$)$_8$—CON(C$_8$H$_{17}$)$_2$.

According to one advantageous embodiment, the esteramide has a melting point that is less than or equal to 20° C., preferably 5° C., preferably 0° C.

Process

The compound of the invention may be prepared by any suitable method. It is especially possible to carry out a step of reacting an anhydride of formula (I') with an alcohol of formula R$^1$—OH and/or an amine of formula HNR$^2$R$^3$:

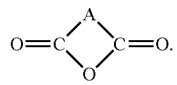
(I')

The anhydride may be prepared during a prior step a) of cyclization of a diacid of formula HOOC-A-COOH, preferably by reaction of the diacid with acetic anhydride. It is possible in particular to implement a reflux in an excess of acetic anhydride. Next it is possible to carry out a condensation of the product of formula (I').

It is possible in particular to carry out one of the following reaction sequences 1) or 2):

Sequence 1):
Step 1b) the anhydride of formula (I') is reacted with an alcohol of formula R$^1$—OH, so as to obtain an ester acid compound of formula (I'') R$^1$—OOC-A-COOH;
Step 1c) the compound of formula (I'') is converted to a compound of formula (I) using an amine of formula HNR$^2$R$^3$;

Sequence 2):
Step 2b) the anhydride of formula (I') is reacted with an amine of formula HNR$^2$R$^3$ so as to obtain an amide acid compound of formula (II''):

Step 2c) the compound of formula (II'') is converted to a compound of formula (I) using an alcohol of formula R$^1$—OH.

Step 1b) is preferably carried out using at least one molar equivalent of alcohol relative to the anhydride. It is possible to use a large excess of alcohol, for example from 2 to 20 equivalents, especially from 5 to 15. It is especially possible to use the alcohol as a solvent for the reaction.

According to one particular embodiment, step 1c) comprises the following steps (which may be simultaneous or subsequent, preferably subsequent):

1c1) the compound of formula (I'') is converted to an acyl chloride of formula (I''') below, preferably by reaction with thionyl chloride:

1c2) the compound of formula (I''') is reacted with the amine of formula NR$^3$R$^4$ so as to obtain the compound of formula (I).

Step 1c2) is accompanied by the formation of hydrochloric acid. It is possible to use a base in order to trap it, for example triethanolamine or triethylamine (TEA). This step may be carried out with at least 0.8 molar equivalent of amine, preferably with at least one equivalent. It is especially possible to use an excess of 1.05 to 1.4 molar equivalents.

According to another useful process for preparing the compound of the invention, a step of reacting a diester of formula R$^1$OOC-A-COOR$^1$ with an amine of formula HNR$^2$R$^3$, then optionally a step of reacting with an alcohol of formula R$^{1'}$—OH, where R$^{1'}$ is a group chosen from the R$^1$ groups mentioned above, but different from the R$^1$ group of the diester, is carried out. This process is particularly advantageous and economical since the diesters are prepared in large quantities and are readily available. It is thus possible to optimize the production processes. It is possible, for example, to carry out the following reaction sequence 3):

Sequence 3)

Step 3a) a diester of formula R$^1$OOC-A-COOR$^1$, preferably of formula MeOOC-A$_{MG}$-COOMe or MeOOC-A$_{ES}$-COOMe is reacted with an amine of formula HNR$^2$R$^3$ so as to obtain a product comprising an esteramide of formula:

preferably R$^1$OOC-A$_{MG}$-CONR$^2$R$^3$ or R$^1$OOC-A$_{ES}$-CONR$^2$R$^3$, preferably MeOOC-A$_{MG}$-CONR$^2$R$^3$ or MeOOC-A$_{ES}$-CONR$^2$R$^3$;

Step 3b) optionally, it is reacted with an alcohol of formula R$^{1'}$—OH so as to obtain a product comprising an esteramide of formula:

preferably R$^{1'}$OOC-A$_{MG}$-CONR$^2$R$^3$ or R$^{1'}$OOC-A$_{ES}$-CONR$^2$R$^3$, where $R^{1'}$ is a group chosen from the $R^1$ groups mentioned above, but different from the $R^1$ group of the diester.

If the initial diester has the $R^1$ group of the desired compound, then step 3b) is generally pointless. If not, this step will typically be carried out. Preferably one starts from the diester having the desired $R^1$ group.

During step 3a), preferably from 0.7 to 1.5 mol, for example 0.8 to 1.2 mol, preferably from 0.9 to 1.1 mol, preferably around 1 mol of amine is used per mole of diester. It is advantageous to operate with a slight excess such as an excess of at least 1.05 mol of amine per mole of diester, for example from 1.05 to 1.1 mol of amine per mole of diester.

Step 3a) may be carried out in solution, for example in aqueous solution, or in solution in a solvent such as toluene or an alcohol. It is preferred to operate in a non-aqueous solution, avoiding any presence of water. It is possible, during this step, to gradually eliminate the methanol formed in order to favor the reaction. The elimination may be accompanied by an elimination of the solvent, for example to an azeotrope. After separation of the methanol, the solvent eliminated may be reintroduced into the process. Step 3a) is preferably carried out in the presence of a catalyst, in particular a basic type catalyst. It is possible, for example, to use methylates such as MeONa, carbonates such as $K_2CO_3$ or $Na_2CO_3$, or titanates.

Step 3b) is a transesterification step. It may especially be catalysed by acids or bases, for example by $K_2CO_3$ or $Na_2CO_3$.

It is noted that in all the processes and sequences mentioned above, it is possible to carry out optional intermediate steps of separation and/or of purification, in order to eliminate undesired by-products. The by-products may optionally be used to manufacture other products, or may be converted in order to be reintroduced into the process.

The reaction may be followed by steps of filtration and/or of purification, for example by distillation.

The diacids, if necessary in the form of mixtures, may especially be obtained from a mixture of dinitrile compounds, if necessary in the form of mixtures. The dinitriles may especially be dinitriles produced and recovered in the process for manufacturing adiponitrile by double hydrocyanation of butadiene. In this case, they may be mixtures of dinitriles. This process, used on a large scale in industry for producing the large majority of adiponitrile consumed in the world, is described in numerous patents and books.

The hydrocyanation reaction of butadiene predominantly leads to the formation of linear dinitriles but also to a formation of branched dinitriles, the two main ones of which are methylglutaronitrile and ethylsuccinonitrile.

In the steps of separating and purifying adiponitrile, the branched dinitrile compounds are separated by distillation and recovered, for example as an overhead fraction in a distillation column.

Diacids that can be used may be obtained by reaction between the dinitrile compounds and a mineral base, to obtain acid salts, then neutralization of these salts by an acid. Diacids that can be used may also be obtained by acid hydrolysis of the dinitrile compounds.

Diesters of formula $R^1OOC$-$A$-$COOR^1$ that can be used for carrying out the sequence 3 are commercially available, in particular from Invista under the references DBE, or from Rhodia under the name Rhodiasolv® RPDE.

Processes for preparing diacids and/or diesters are especially described in documents WO 2007/101929, FR 2902095, WO 2008/009792, WO 2008/062058.

Uses—Formulations

The compound of the invention and/or a composition of matter comprising it described above may especially be used as a solvent, co-solvent and/or crystallization inhibitor or as a coalescing agent.

The term "co-solvent" is understood to mean that other solvents may be combined with it. The use as a solvent or co-solvent in particular comprises the use for dissolving a compound in a formulation, in a reaction medium, the use for completely or partially dissolving a product to be eliminated (degreasing, stripping), and/or for facilitating the detachment of films of matter.

The compound of the invention and/or a composition of matter comprising it described above, may especially be used, for the functions indicated above or for other functions, in a phytosanitary formulation, in a cleaning formulation, in a stripping formulation, in a degreasing formulation, in a lubricant or textile formulation, in a coating formulation, for example in a paint formulation or in a pigment or ink formulation.

The compound may, for example, be used as a coalescing agent in an aqueous paint formulation.

The compound may especially be used as a degreasing agent on metallic surfaces, for example the surfaces of tools, of manufactured articles, of sheets, of moulds, especially made of steel or made of aluminium or made of alloys of these metals.

The compound may especially be used as a cleaning solvent on hard surfaces or textile surfaces.

The compound may especially be used as a stripping solvent for paint or resins, on the surfaces of tools, for example foundry moulds, on the surfaces of industrial sites (floors, partitions, etc.).

The cleaning and/or degreasing formulations may especially be household care formulations, used in homes or in public areas (hotels, offices, factories, etc.). They may be formulations for cleaning hard surfaces such as floors, the surfaces of furniture and of kitchen and bathroom fittings, or dishes. These formulations may also be used in the industrial sphere for degreasing manufactured products and/or for cleaning them.

In the context of uses in reaction media, mention is especially made of the use, in the context of solution polymerization, in particular for the preparation, in solution, of polycondensates, especially polyimides or polyesters or polyamides or polyamide-imides, especially partially or completely aromatic polycondensates such as aromatic polyamides (aramids).

The compound of the invention and/or a composition of matter comprising it described above, may especially be used in phytosanitary formulations comprising a solid active product. More details are given below, where the word "solvent" may denote the compound of the invention or a composition of matter comprising it, described above.

Detailed Use in the Context of Phytosanitary Formulations

The phytosanitary formulation is generally a concentrated phytosanitary formulation comprising an active compound.

Agriculture uses many active substances such as fertilizers or pesticides, for example insecticides, herbicides or fungicides. These are referred to as active phytosanitary products (or phytosanitary products having an active substance). Active phytosanitary products are generally produced in pure or very concentrated form. They must be used on farms at low concentrations. For this purpose, they are generally formulated with other ingredients in order to enable an easy dilution by weight by the farmer. These are referred to as phytosanitary formulations. The dilution made by the farmer is generally carried out by mixing the phytosanitary formulation with water.

Thus the phytosanitary formulations must allow an easy dilution by weight by the farmer, in order to obtain a product in which the phytosanitary product is correctly dispersed, for example in the form of a solution, emulsion, suspension or a suspo-emulsion. The phytosanitary formulations thus allow the transport of a phytosanitary product in a relatively concentrated form, easy packaging and/or easy handling by the final user. Various types of phytosanitary formulations may be used depending on the various phytosanitary products. Mention is made, for example, of emulsifiable concentrates (ECs), emulsions in water (EW), microemulsions (MEs), wettable powders (WPs), and water dispersible granules (WDGs). The formulations that it is possible to use depend on the physical form of the phytosanitary product (for example, solid or liquid), and on its physicochemical properties in the presence of other compounds such as water or solvents.

After dilution by weight by the farmer, for example by mixing with water, the phytosanitary product may be in various physical forms: solution, dispersion of solid particles, dispersion of droplets of product, droplets of solvent in which the product is dissolved, etc. The phytosanitary formulations generally comprise compounds that make it possible to obtain these physical forms. These may be, for example, surfactants, solvents, mineral supports and/or dispersants. Very often these compounds do not have an active nature, but an intermediate nature of assistance to the formulation. The phytosanitary formulations may especially be in liquid form or in solid form.

In order to prepare phytosanitary formulations of solid active phytosanitary products, it is known to dissolve the product in a solvent. The phytosanitary formulation thus comprises a solution of the product in the solvent. The formulation may be in solid form, for example in the form of a wettable powder (WP) where the solution saturates an inorganic support, for example of kaolin and/or of silica. The formulation may alternatively be in liquid form, for example in the form of an emulsifiable concentrate (EC) having a single clear liquid phase comprising the solvent and the product in solution, which may form an emulsion by addition of water, without stirring or with gentle stirring. It may also be in the form of a cloudy emulsion in water (EW), the dispersed phase of which in the water comprises the solvent and the product in solution in the solvent. It may also be in the form of a clear microemulsion (ME), the dispersed phase of which in the water comprises the solvent and the product in solution in the solvent.

Certain solid phytosanitary active agents are often difficult to formulate. For example, tebuconazole is a particularly effective fungicide of widespread use especially for cultivating soybeans. For certain phytosanitary active agents, it is difficult to produce concentrated formulations, that are easy for the farmer to dilute, that are stable and that are without substantial (known or perceived) drawbacks as regards safety, toxicity and/or ecotoxicity. For certain active agents, it is difficult to formulate them at relatively high concentrations with sufficient stability. In particular, it is necessary to prevent the appearance of crystals in particular at low temperature and/or during dilution and/or during storage at high temperature of the diluted composition. The crystals may have negative effects, in particular blocking the filters of the devices used to spread the diluted composition, blocking the spraying devices, reducing the overall activity of the formulation, creating needless problems for waste companies in terms of eliminating the crystals, and/or causing poor distribution of the active product over the agricultural field.

The formulations comprising the solvent have, in particular:
a solubilization of large amounts of active agents;
an absence of crystallization, even for demanding conditions;
a good biological activity which may be due to a good solvation; and/or
a safety, toxicology and/or ecotoxicology profile perceived to be favourable.

The phytosanitary formulation may also be a concentrated phytosanitary formulation comprising:
a) an active phytosanitary product;
b) the solvent (esteramide compound);
c) optionally at least one emulsifier, preferably a surfactant; and
d) optionally water.

Active Phytosanitary Product a)

Active phytosanitary products, especially products that are solid and that are insoluble in water, are known to a person skilled in the art. The active phytosanitary product may especially be a herbicide, an insecticide, an acaricide, a fungicide or a rodenticide, for example a raticide.

As non-limiting examples of suitable active ingredients, mention may be made, inter alia, of Ametryne, Diuron, Linuron, Chlortoluron, Isoproturon, Nicosulphuron, Metamitron, Diazinon, Aclonifen, Atrazine, Chlorothalonil, Bromoxynil, Bromoxynil heptanoate, Bromoxynil octanoate, Mancozeb, Manebe, Zineb, Phenmedipham, Propanyl, the phenoxyphenoxy series, the heteroaryloxyphenoxy series, CMPP, MCPA, 2,4-D, Simazine, the active products of the imidazolinone series, the organophosphorus family especially including Azinphos-ethyl, Azinphos-methyl, Alachlore, Chlorpyriphos, Diclofop-methyl, Fenoxaprop-p-ethyl, Methoxychlore, Cypermethrine, Fenoxycarbe, cymoxanil, chlorothalonyl, neonicotinoid insecticides, the family of triazole fungicides such as azaconazole, bromuconazole, cyproconazole, difenoconazole, diniconazole, epoxyconazole, fenbuconazole, flusilazole, myclobutanyl, tebuconazole, triadimefon, triadimenol, strobilurines such as pyraclostrobine, picoxystrobine, azoxystrobine, famoxadone, kresoxym-methyl and trifloxystrobine, sulphonylureas such as bensulphuron-methyl, chlorimuron-ethyl, chlorsulphuron, metsulphuron-methyl, nicosulphuron, sulphomethuron-methyl, triasulphuron, tribenuron-methyl.

From this list the water-insoluble products are chosen.

The following active phytosanitary products may especially be used:

Alachlor
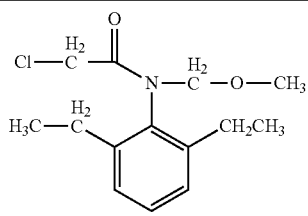
Chlorpyrifos
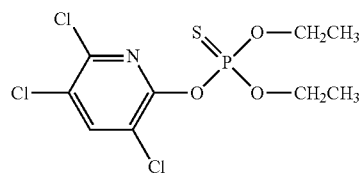 [SMILES: CCOP(=S)(OCC)Oc1nc(Cl)c(Cl)cc1Cl]
Alpha-cypermethrine
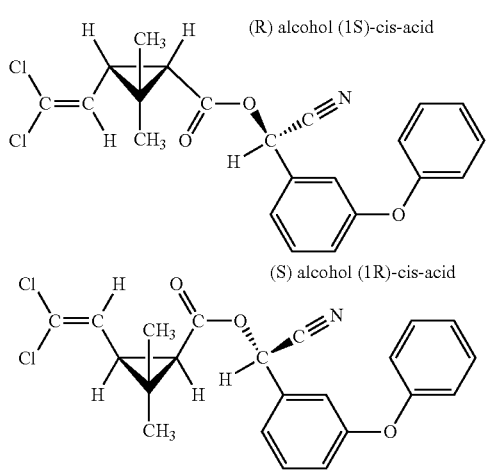
As a racemic mixture and/or as isolated stereoisomers
Phenmedipham
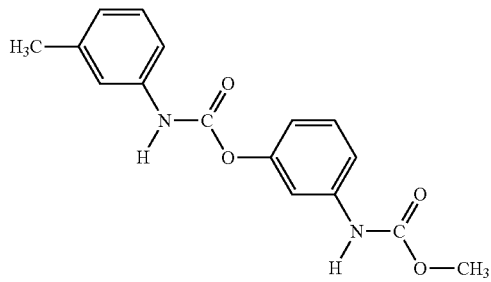
Propanil
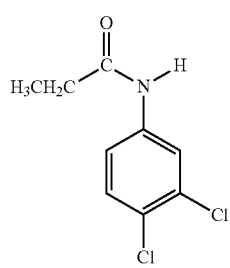
Pendimethalin
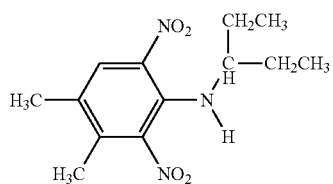 [SMILES: CCC(CC)Nc1c([N+](=O)[O-])cc(C)c(C)c1[N+](=O)[O-]]

-continued
Triadimenol
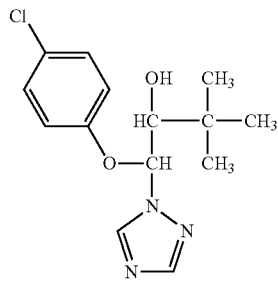 [SMILES: CC(C)(C)C(O)C(Oc1ccc(Cl)cc1)n1cncn1]
Trifluralin
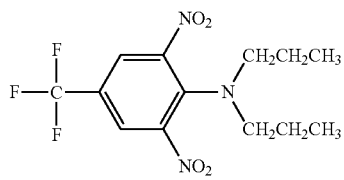
Oxyfluorfen
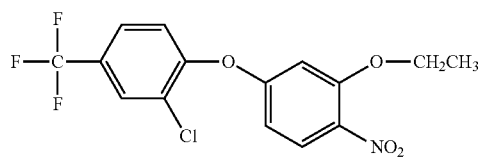 [SMILES: CCOc1cc(Oc2ccc(C(F)(F)F)cc2Cl)ccc1[N+](=O)[O-]]
Dimethoate
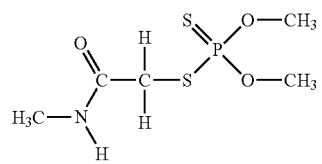
Imidacloprid
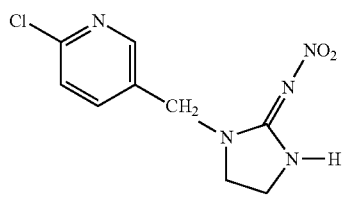 [SMILES: O=[N+]([O-])N=C1NCCN1Cc1ccc(Cl)nc1]
Proxopur
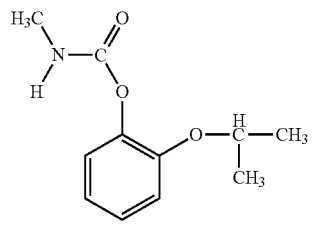
Benomyl
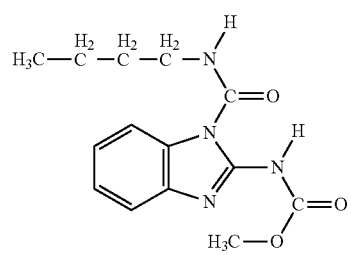

-continued
Deltamethrine
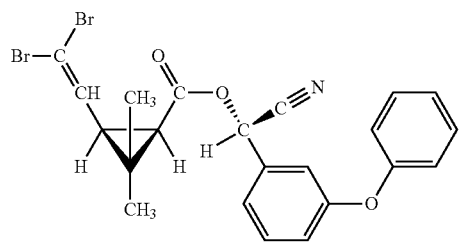 [SMILES: CC1(C)[C@H](C(=O)O[C@H](C#N)c2cccc(Oc3ccccc3)c2)[C@@H]1C=C(Br)Br]
Fenvalerate
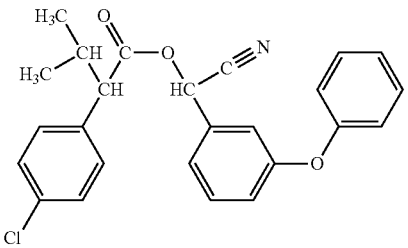 [SMILES: CC(C)C(C(=O)OC(C#N)c1cccc(Oc2ccccc2)c1)c1ccc(Cl)cc1]
Abamectin
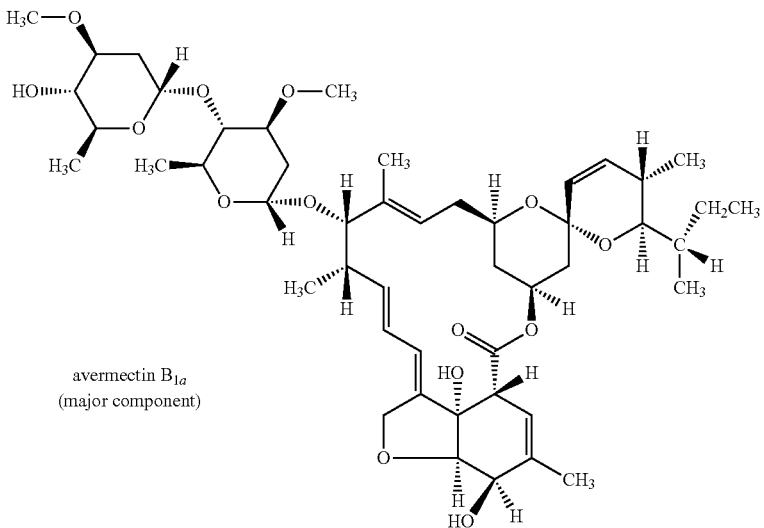 [SMILES: CC[C@H](C)[C@H]1O[C@]2(C=C[C@@H]1C)C[C@@H]1C[C@@H](C/C=C(\C)[C@@H](O[C@H]3C[C@H](OC)[C@@H](O[C@H]4C[C@H](OC)[C@@H](O)[C@H](C)O4)[C@H](C)O3)[C@@H](C)/C=C/C=C3\CO[C@@H]4[C@H](O)C(C)=C[C@@H](C(=O)O1)[C@]34O)O2]
avermectin B$_{1a}$
(major component)
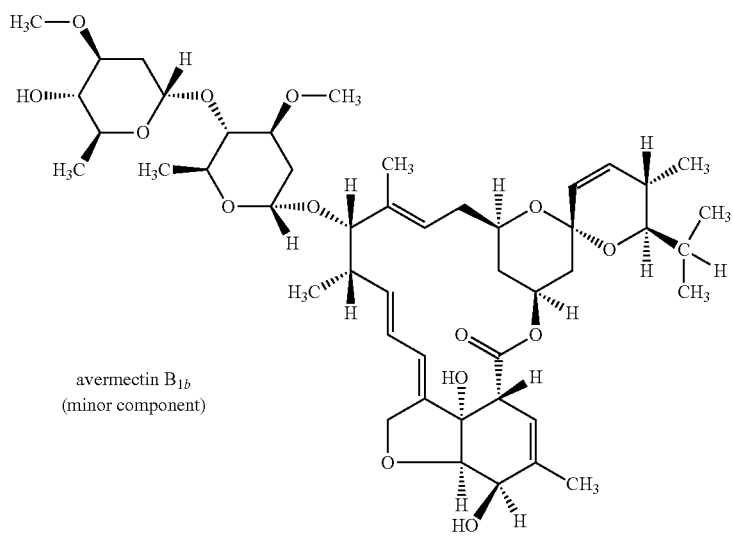 [SMILES: CO[C@H]1C[C@H](O[C@H]2[C@H](C)O[C@@H](O[C@@H]3/C(C)=C/C[C@@H]4C[C@@H](C[C@]5(C=C[C@H](C)[C@@H](C(C)C)O5)O4)OC(=O)[C@@H]4C=C(C)[C@@H](O)[C@H]5OC/C(=C\C=C\[C@@H]3C)[C@]54O)C[C@@H]2OC)O[C@@H](C)[C@@H]1O]
avermectin B$_{1b}$
(minor component)

-continued
Amicarbazone 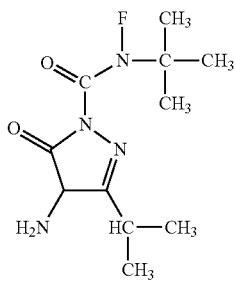 [SMILES: CC(C)C1=NN(C(=O)N(F)C(C)(C)C)C(=O)C1N]
Bifenthrin 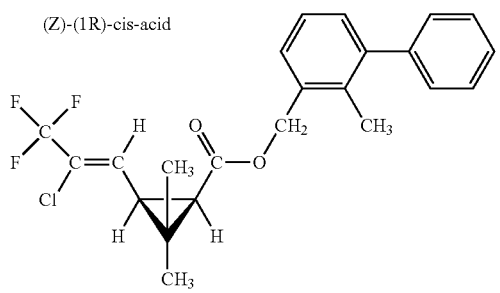 [SMILES: Cc1c(COC(=O)[C@@H]2[C@H](/C=C(\Cl)C(F)(F)F)C2(C)C)cccc1-c1ccccc1]
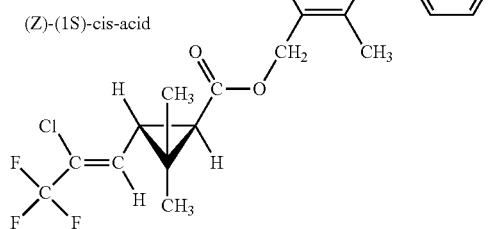
Carbosulphan 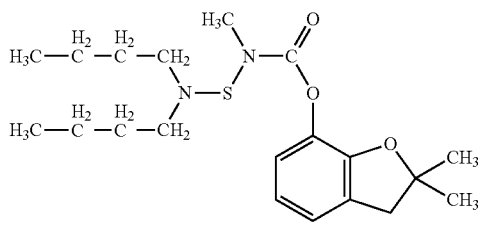 [SMILES: CCCCN(CCCC)SN(C)C(=O)Oc1cccc2c1OC(C)(C)C2]
Cyfluthrin 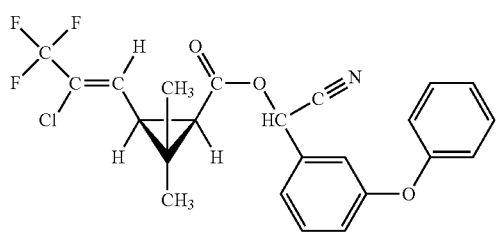
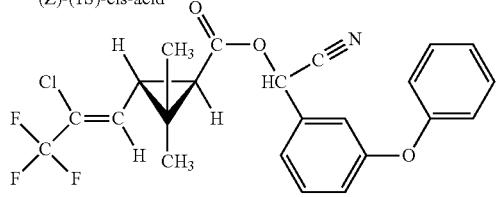

-continued
Difenconazole 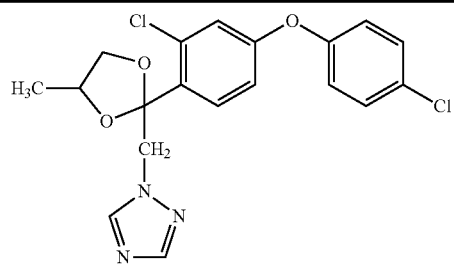
Ethofenprox 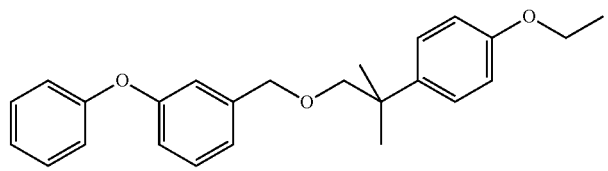 [SMILES: CCOc1ccc(C(C)(C)COCc2cccc(Oc3ccccc3)c2)cc1]
Fenoxapropethyl 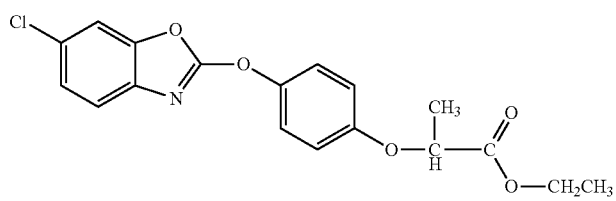 [SMILES: CCOC(=O)C(C)Oc1ccc(Oc2nc3ccc(Cl)cc3o2)cc1]
Fipronil 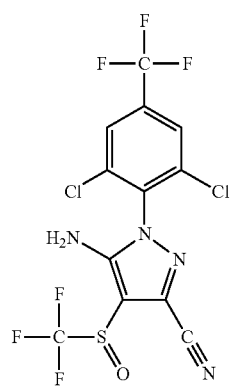 [SMILES: N#Cc1nn(-c2c(Cl)cc(C(F)(F)F)cc2Cl)c(N)c1S(=O)C(F)(F)F]
Fenvalerate 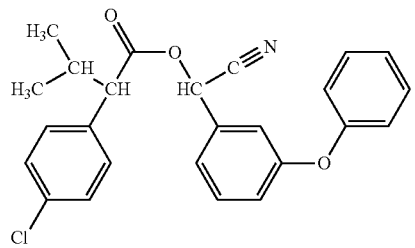 [SMILES: CC(C)C(C(=O)OC(C#N)c1cccc(Oc2ccccc2)c1)c1ccc(Cl)cc1]
Fluazifop-p-butyl 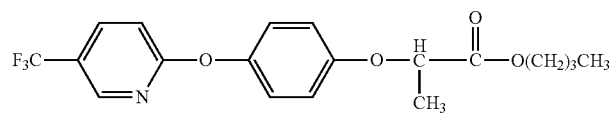
Flfenouron 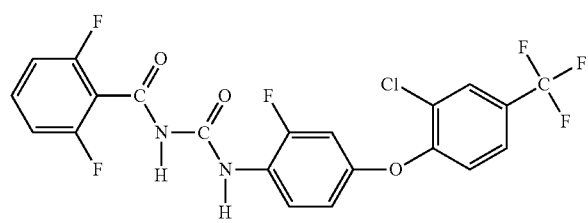 [SMILES: O=C(NC(=O)c1c(F)cccc1F)Nc1ccc(Oc2ccc(C(F)(F)F)cc2Cl)cc1F]

| | | |
|---|---|---|
| Hexazinone | 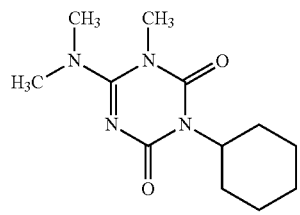 [SMILES: CN(C)c1nc(=O)n(C2CCCCC2)c(=O)n1C] | |
| Lambda-cyalothrin | 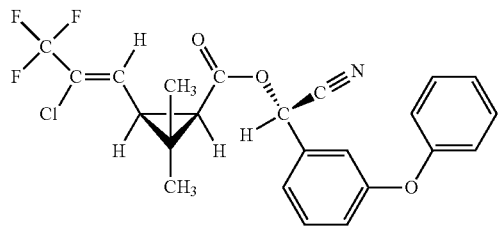 | (S)-alcohol (Z)-(1R)-cis-acid |
| | 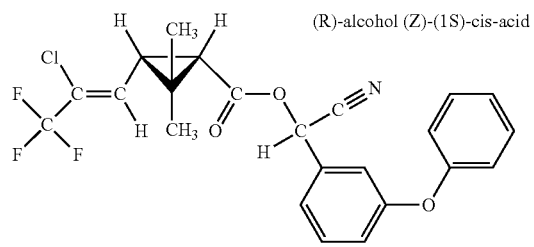 [SMILES: CC1(C)[C@H](/C=C(\Cl)C(F)(F)F)[C@@H]1C(=O)OC(C#N)c1cccc(Oc2ccccc2)c1] | (R)-alcohol (Z)-(1S)-cis-acid |
| Methomyl | 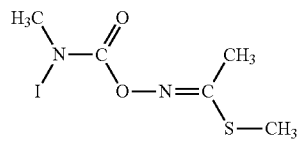 | |
| Permethrin | 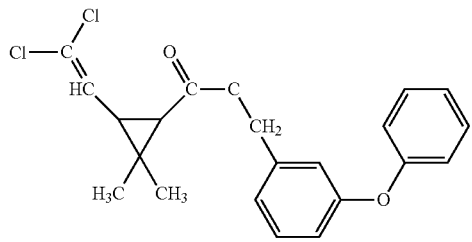 [SMILES: CC1(C)C(C=C(Cl)Cl)C1C(=O)CCc1cccc(Oc2ccccc2)c1] | |
| Prochloraz | 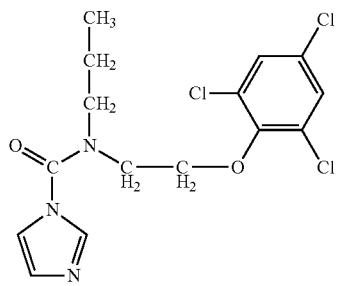 [SMILES: CCCN(CCOc1c(Cl)cc(Cl)cc1Cl)C(=O)n1ccnc1] | |

Propiconazole 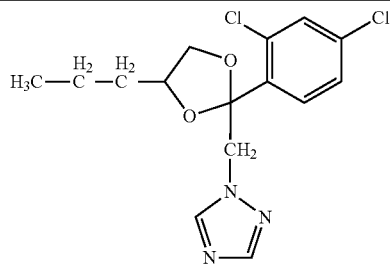

Tebuconazole 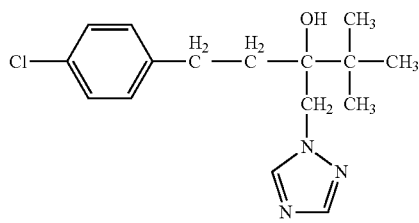 [SMILES: CC(C)(C)C(O)(CCc1ccc(Cl)cc1)Cn1cncn1]

These products and names are known to a person skilled in the art. It is possible to combine several active phytosanitary products.

Emulsifier c)

The phytosanitary formulation may comprise an emulsifier, typically and preferably a surfactant. Emulsifiers are agents intended to facilitate the emulsifying or the dispersion after bringing the formulation into contact with water, and/or intended to stabilize (over time and/or at temperature) the emulsion or the dispersion, for example by avoiding sedimentation.

Surfactants are known compounds, that have a generally relatively low molecular weight, for example of less than 1000 g/mol. The surfactant may be an anionic surfactant in salified or acid form, a preferably polyalkoxylated non-ionic surfactant, a cationic surfactant or an amphoteric surfactant (term that also includes zwitterionic surfactants). It may be a mixture or a combination of these surfactants.

Examples of anionic surfactants that may be mentioned, without wishing to be limited thereto, include:

alkylsulphonic acids or arylsulphonic acids, optionally substituted with one or more hydrocarbon-based groups, and the acid function of which is partially or totally salified, for instance $C_8$-$C_{50}$, more particularly $C_8$-$C_{30}$ and preferably $C_{10}$-$C_{22}$ alkylsulphonic acids, benzenesulphonic acids or naphthalenesulphonic acids substituted with one to three $C_1$-$C_{30}$, preferably $C_4$-$C_{16}$ alkyl and/or $C_2$-$C_{30}$, preferably $C_4$-$C_{16}$ alkenyl groups, alkylsulphosuccinic acid monoesters or diesters, the linear or branched alkyl part of which is optionally substituted with one or more linear or branched $C_2$-$C_4$ hydroxylated and/or alkoxylated (preferably ethoxylated, propoxylated or ethopropoxylated) groups, phosphate esters chosen more particularly from those comprising at least one linear or branched, saturated, unsaturated or aromatic hydrocarbon-based group containing 8 to 40 and preferably 10 to 30 carbon atoms, optionally substituted with at least one alkoxylated (ethoxylated, propoxylated or ethopropoxylated) group. In addition, they comprise at least one monoesterified or diesterified phosphate ester group such that one or two free or partially or totally salified acid groups may be present. The preferred phosphate esters are of the type such as monoesters and diesters of phosphoric acid and of alkoxylated (ethoxylated and/or propoxylated) mono-, di- or tristyrylphenol, or of alkoxylated (ethoxylated and/or propoxylated) mono-, di- or trialkylphenol, optionally substituted with one to four alkyl groups; of phosphoric acid and of an alkoxylated (ethoxylated or ethopropoxylated) $C_8$-$C_{30}$ and preferably $C_{10}$-$C_{22}$ alcohol; of phosphoric acid and of a non-alkoxylated $C_8$-$C_{22}$ and preferably $C_{10}$-$C_{22}$ alcohol.

sulphate esters obtained from saturated or aromatic alcohols, optionally substituted with one or more alkoxylated (ethoxylated, propoxylated or ethopropoxylated) groups, and for which the sulphate functions are in free or partially or totally neutralized acid form. Examples that may be mentioned include the sulphate esters obtained more particularly from saturated or unsaturated $C_8$-$C_{20}$ alcohols, which may comprise 1 to 8 alkoxylated (ethoxylated, propoxylated or ethopropoxylated) units; the sulphate esters obtained from polyalkoxylated phenol, substituted with 1 to 3 saturated or unsaturated $C_2$-$C_{30}$ hydrocarbon-based groups, and in which the number of alkoxylated units is between 2 and 40; the sulphate esters obtained from polyalkoxylated mono-, di- or tristyrylphenol in which the number of alkoxy units ranges from 2 to 40.

The anionic surfactants may be in acid form (they are potentially anionic) or in a partially or totally salified form, with a counterion. The counterion may be an alkali metal, such as sodium or potassium, an alkaline-earth metal, such as calcium, or an ammonium ion of formula $N(R)_4^+$ in which the R groups, which may be identical or different, represent a hydrogen atom or a $C_1$-$C_4$ alkyl radical optionally substituted with an oxygen atom.

Examples of nonionic surfactants that may be mentioned, without wishing to be limited thereto, include:

polyalkoxylated (ethoxylated, propoxylated or ethopropoxylated) phenols substituted with at least one $C_4$-$C_{20}$ and preferably $C_4$-$C_{12}$ alkyl radical, or substituted with at least one alkylaryl radical, the alkyl part of which is $C_1$-$C_6$. More particularly, the total number of alkoxy units is between 2 and 100. Examples that may be mentioned include polyalkoxylated mono-, di- or tri(phenylethyl)phenols, or polyalkoxylated nonylphenols. Among the ethoxylated and/or propoxylated, sulphated and/or phosphated di- or tristyrylphenols, mention may be made of ethoxylated bis(1-phenylethyl)phenol, containing 10 oxyethylene units, ethoxylated bis(1-phenylethyl)phenol, containing 7 oxyethylene units, ethoxylated sulphated bis(1-phenylethyl)phenol, containing 7 oxyethylene units, ethoxylated tris(1-phenylethyl)phenol, containing 8 oxyethylene units, ethoxylated tris(1-phenylethyl)phenol containing 16 oxyethylene units, ethoxylated sulphated tris (1-phenylethyl)phenol, containing 16 oxyethylene units, ethoxylated tris(1-phenylethyl)phenol, containing 20 oxyethylene units, and ethoxylated phosphated tris(1-phenylethyl) phenol, containing 16 oxyethylene units, polyalkoxylated (ethoxylated, propoxylated or ethopropoxylated) $C_6$-$C_{22}$ fatty alcohols or fatty acids. The number of alkoxy units is between 1 and 60. The term "ethoxylated fatty acid" includes both the products obtained by ethoxylation of a fatty acid with ethylene oxide and those obtained by esterification of a fatty acid with a polyethylene glycol, polyalkoxylated (ethoxylated, propoxylated or ethopropoxylated) triglycerides of plant or animal origin. Triglycerides derived from lard, tallow, groundnut oil, butter oil, cottonseed oil, linseed oil, olive oil, palm oil, grapeseed oil, fish oil, soybean oil, castor oil, rapeseed oil, copra oil or coconut oil, and comprising a total number of alkoxy units of between 1 and 60, are thus suitable for use. The term "ethoxylated triglyceride" is directed both toward the products obtained by ethoxylation of a triglyceride with ethylene oxide and toward those obtained by transesterification of a triglyceride with a polyethylene glycol, optionally polyalkoxylated (ethoxylated, propoxylated or ethopropoxylated) sorbitan esters, more particularly cyclized sorbitol esters of $C_{10}$ to $C_{20}$ fatty acids, for instance lauric acid, stearic acid or oleic acid, and comprising a total number of alkoxy units of between 2 and 50.

Emulsifiers that can be used are especially the following products, all sold by Rhodia:

Soprophor® TSP/724: surfactant based on ethopropoxylated tristyrylphenol;

Soprophor® 796/O: surfactant based on ethopropoxylated tristyrylphenol;

Soprophor® CY 8: surfactant based on ethoxylated tristyrylphenol;

Soprophor® BSU: surfactant based on ethoxylated tristyrylphenol;

Alkamuls® RC: surfactant based on ethoxylated castor oil;

Alkamuls® OR/36: surfactant based on ethoxylated castor oil;

Alkamuls® T/20: surfactant based on a sorbitan ester.

The formulation advantageously comprises at least 4%, preferably at least 5%, preferably at least 8%, by weight of solids of at least one surfactant c).

It is mentioned that the solvent may be combined with an aromatic and/or non-aromatic surfactant.

Other Details Relating to the Phytosanitary Formulation

The concentrated phytosanitary formulation preferably does not comprise large amounts of water. Typically, the water content is less than 50% by weight, advantageously less than 25% by weight. It will generally be less than 10% by weight.

The formulation is preferably a liquid formulation, for example in the form of an emulsifiable concentrate (EC), an emulsion in water (EW) or a microemulsion (ME). In this case, it preferably comprises less than 500 g/l of water, more preferably less than 250 g/l. It will generally be less than 100 g/l.

The formulations may advantageously comprise:
a) from 4 to 60%, preferably from 10 to 50%, of the phytosanitary product, by weight of active ingredient;
b) from 10 to 92%, preferably from 20 to 80%, of solvent, by weight;
c) from 4 to 60%, preferably from 5 to 50%, preferably from 8 to 25%, by weight of solids, of an emulsifier, preferably of a surfactant; and
d) from 0 to 10% by weight of water.

The production of solid formulations, for example formulations in which a liquid comprising the phytosanitary product solubilized in the solvent is supported by a mineral and/or dispersed in a solid matrix, is not ruled out.

The formulation may of course comprise ingredients (or "additives") other than the active phytosanitary product, the solvent(s), the optional emulsifier(s) and the optional water. It may especially comprise viscosity modifiers, anti-foaming agents, especially silicone-based anti-foaming agents, anti-rebound agents, agents for preventing wash-off, inert fillers, especially mineral fillers, anti-gelling agents, etc.

In particular, the formulations may comprise additives, known as other additives, that do not come under the definition of the products a), b), or c), such as:

other solvents, generally in a small amount, for example an amount less than the amount of compound of formula (I). As other solvents, mention is especially made of solvents from the family of phosphates, phosphonates or phosphine oxides such as TEBP, TBP, TEPO or DBBP. Mention is also made of alkyldimethylamides where the alkyl is a $C_6$-$C_{18}$ alkyl, especially those sold under the trade mark Genagen. Mention is also made of lactate esters, especially those sold under the trade mark Purasolv. Mention is also made of fatty acid methyl esters, especially those sold under the trade mark Phytorobe. Mention is also made of dibasic esters, especially those sold by Rhodia under the trade marks Rhodiasolv RPDE and Rhodiasolv DIB. Mention is also made of hydrocarbon cups, cyclic amides such as NMP, and lactones. Mention is also made of the bis(dialkylamides) described in document WO 2008/074837.

crystallization inhibitors. These may be the solvents mentioned above. They may also be non-polyalkoxylated fatty alcohols or fatty acids. Mention is made, for example, of the product Alkamuls® OL700 sold by Rhodia.

Conventional processes for preparing phytosanitary formulations or mixtures of solvents may be used. The process may be carried out by simple mixing of the constituents.

The concentrated phytosanitary formulation is intended to be spread over a cultivated field or field to be cultivated, for example a field of soybean, usually after dilution in water, in order to obtain a diluted composition. The dilution is generally carried out by the farmer, directly in a tank ("tank-mix"), for example in the tank of a device intended to spread the composition. It is not ruled out that the farmer adds other phytosanitary products, for example fungicides, herbicides, pesticides, insecticides or fertilizers. Thus, the formulation may be used to prepare a composition, diluted in water, of the active phytosanitary product by mixing at least one part by weight of concentrated formulation with at least 10 parts of water, preferably less than 1000 parts. The dilution ratios and the amounts to be applied to the field generally depend on the phytosanitary product and the desirable dose for treating the field; this may be determined by the farmer.

Other details or advantages will become apparent in light of the examples that follow, which are in no way limiting.

EXAMPLES

General Processing Procedures for the Synthesis of Esteramides

Procedure A: Formation of the Ester Acid

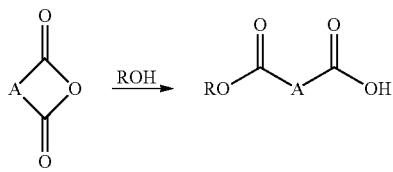

The cyclic anhydride is mixed with the alcohol and heated at 60° C. for 3 h. The volatiles are drawn off by distillation under reduced pressure if necessary. The final product can be purified by distillation under reduced pressure.

Procedure B: Formation of the Ester/Acid Chloride

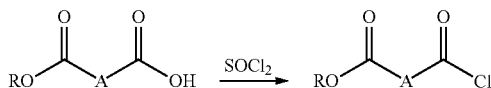

The ester acid and the thionyl chloride are mixed at ambient temperature. The reaction mixture may be heated under reflux to complete the reaction. The volatile species are drawn off by distillation under reduced pressure to obtain the crude product, which is typically used as is without any form of purification.

Procedure C: Formation of the Esteramide

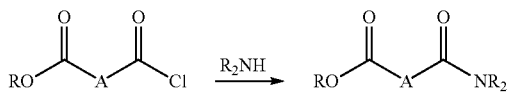

Toluene and trimethylamine (TEA) are mixed under an inert atmosphere and cooled to −20° C. Dimethylamine (DMA) is then added. The ester/acid chloride is added slowly so as to keep the temperature below 0° C. The mixture is then stirred at ambient temperature overnight then filtered to remove the precipitate. The filtrate is evaporated under vacuum to obtain the crude product. The final product is obtained by distillation under reduced pressure of the reaction crude.

Procedure D: Formation of the Amide Acid

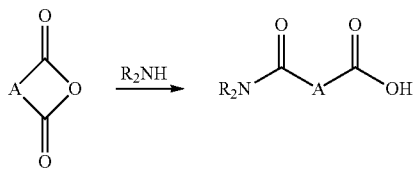

The cyclic anhydride is added to the primary amine while keeping the temperature below 40° C. The mixture is then kept at ambient temperature for 10-24 h. The volatile species are evaporated under vacuum. The product may be purified by distillation under reduced pressure.

Procedure E: Formation of the Esteramide

The amide acid and the alcohol are mixed at ambient temperature, then the thionyl chloride is added slowly so as to keep the temperature below 30° C. The hydrochloric acid formed during the reaction may be trapped by a concentrated sodium hydroxide solution. The reaction mixture is stirred at ambient temperature until the initial products have been consumed. The reaction may be monitored by GC. The volatile species are evaporated under vacuum to obtain the crude product. In some cases, the crude is dissolved in methanol and the pH adjusted to around 6-7 before evaporation of the solvent. The final product is then obtained after distillation under reduced pressure.

Procedure F: Preparation of the Cyclic Anhydride of 2-MGA

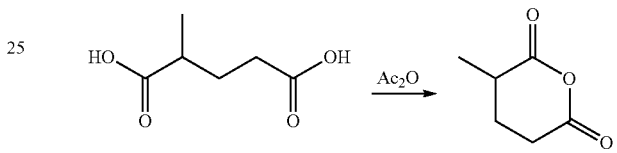

Raw Materials

| 2-Methyl glutaric acid (2-MGA) | Acetic anhydride |
|---|---|
| 327 g; 2.23 mol; Mw: 146.14 | 500 ml; 4.9 mol; 2.2 eq. Mw: 102.09 |

The pure 2-MGA and the acetic anhydride are mixed and heated under reflux (140° C.) for 7 h. The excess acetic anhydride and the acetic acid formed are evaporated under vacuum to obtain the reaction crude (320 g). The oil thus obtained is distilled under reduced pressure (120° C./310 Pa) to obtain a white solid (263 g).

Yield=92.2%

Example 1.1

Preparation of MeOOC—CH$_2$—CH$_2$—CONMe$_2$

The synthesis route was the following:

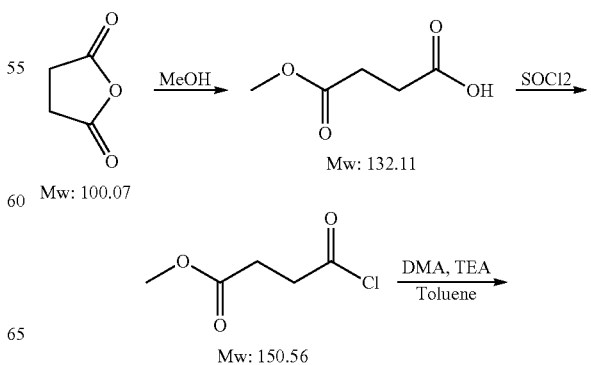

-continued

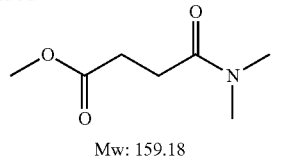

Mw: 159.18

Step 1:
Raw Materials

| Cyclic anhydride | Methanol (anhydrous) |
|---|---|
| 250 g; 2.473 mol; Mw: 100.07; 99% | 1000 ml; 24.73 mol, Mw: 32.04; 10 eq |

The ester acid was obtained by Procedure A.
Final product=311 g, Yield=94%.
Analysis by GC (gas chromatography): area>99%.

Step 2
Raw Materials

| Ester acid | Thionyl chloride |
|---|---|
| 311 g; 2.331 mol; Mw: 132.11; GC: (area) = 99.03% | 340 ml; 4.662 mol; Mw: 118.97, 2 eq |

The ester/acid chloride was obtained by Procedure B.
Crude product=348 g

Step 3
Raw Materials

| Ester/acid chloride | DMA | TEA | Toluene |
|---|---|---|---|
| 348 g; 2.311 mol; 1 eq. Mw: 150.56 | 280 ml; 4.22 mol, 1.83 eq, Mw: 45.08 | 390 ml; 2.80 mol, 1.2 eq; Mw: 101.2 | 1750 + 500 ml |

The esteramide was obtained by Procedure C.
Crude product=402 g
Final product=218 g
GC analysis (area)>98%

Example 1.2

Preparation of MeOOC—CH$_2$—CH$_2$—CH$_2$—CONMe$_2$

The synthesis route was the following:

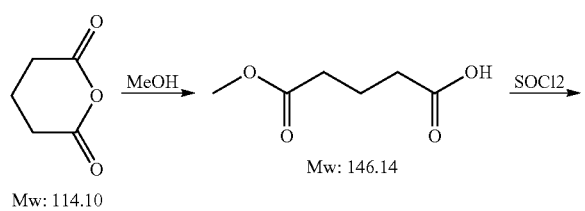

-continued

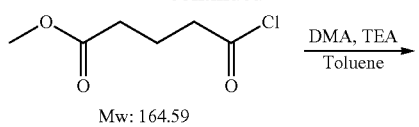

Mw: 164.59

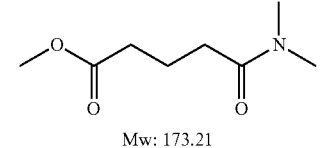

Mw: 173.21

Step 1
Raw Materials

| Cyclic anhydride | Methanol |
|---|---|
| 257 g; 2.2 mol; 1 eq. Mw: 114.10; (GC: 97.89%) | 4350 ml; 107.4 mol; 48.8 eq. Mw: 32.04 |

The ester acid was obtained by Procedure A.
Crude product=333 g (yellow liquid)
Final product=274 g
Analysis by GC (gas chromatography): area>99%

Step 2
Raw Materials

| Ester acid | Thionyl chloride |
|---|---|
| 274 g; 1.869 mol; 1 eq. Mw: 114.10; (GC: 99.68%) | 273 ml; 3.738 mol; 2 eq. Mw: 118.97 |

The ester/acid chloride was obtained by Procedure B.
Crude product=314 g (red liquid), Yield>99%.

Step 3
Raw Materials

| Ester/acid chloride | DMA | TEA | Toluene |
|---|---|---|---|
| 314 g; 1.869 mol; 1 eq. Mw: 164.59 (if 100%) | 250 ml; 3.738 mol, 2 eq, Mw: 45.08; d = 0.68 | 227 ml; 2.243 mol, 1.2 eq, Mw: 101.19; d = 0.726 | 1250 + 500 ml |

The esteramide was obtained by Procedure C.
Crude product=339 g
Final product=237 g, Yield=89.6%
GC analysis (area)>99%

Example 1.3

Preparation of MeOOC-A$_{MG}$-CONMe$_2$ Via a First Route

The synthesis route was the following:

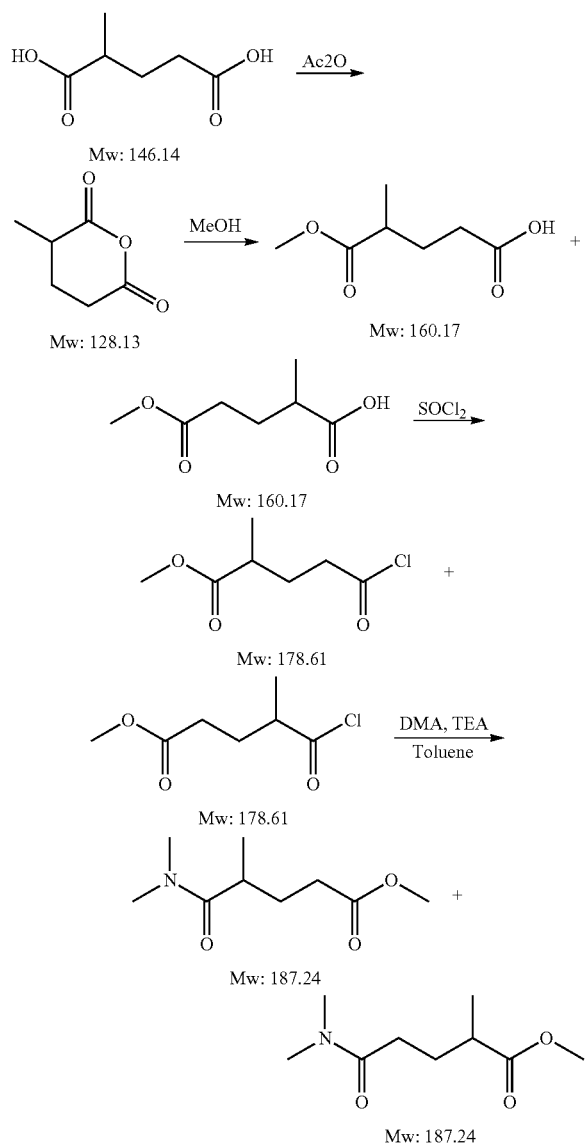

Step 1
Raw Materials

| Cyclic anhydride | Methanol |
|---|---|
| 245 g; 1.91 mol; Mw: 128.13; GC >99% | 1500 ml |

The anhydride was obtained by Procedure F.
The acid ester was obtained by Procedure A.
Crude product=302 g
Final product=261 g, Yield=85.6%
Analysis by GC (gas chromatography): area>99% (isomers 58/42)

Step 2
Raw Materials

| Ester acid | Thionyl chloride |
|---|---|
| 261 g; 1.432 mol, Mw: 160.17, | 240 ml; 2.86 mol; 2 eq. Mw: 118.97 |

The ester/acid chloride was obtained by Procedure B.
Crude product=290 g (yellow liquid)

Step 3
Raw Materials

| Ester/acid chloride | DMA | TEA | Toluene |
|---|---|---|---|
| 290 g; 1.62 mol; Mw: 178.61 | 218 ml; 3.24 mol, 2 eq; Mw: 45.08 | 284 ml; 2.02 mol; 1.25 eq; Mw: 101.19 | 2000 ml |

The methyl ester dimethylamide was obtained by Procedure C.
Crude product=303 g (red liquid)
Final product, GC analysis (area)>99% (isomers 63/37)

Example 1.4

Preparation of MeOOC-A$_{MG}$-CONMe$_2$ Via a Second Route

The synthesis route was the following:

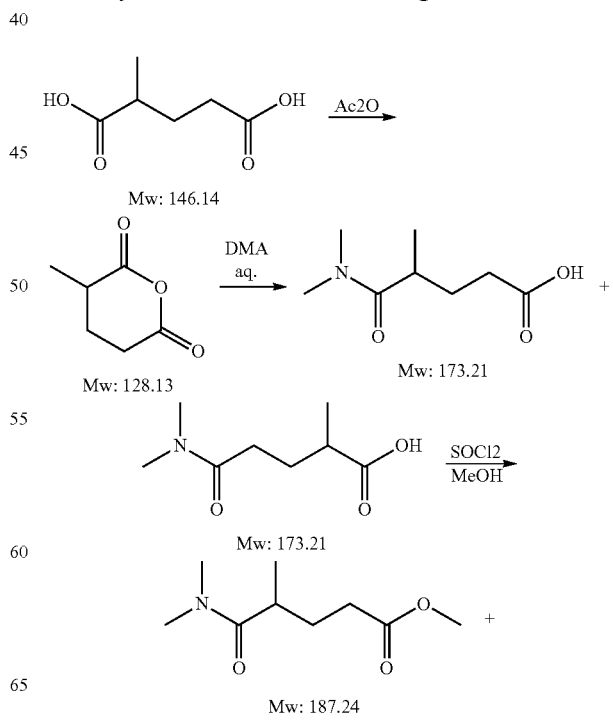

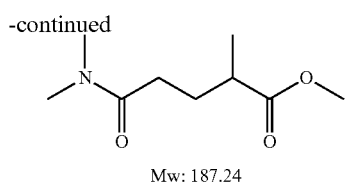

Mw: 187.24

Step 1
Raw Materials

| Cyclic anhydride | DMA aq. |
|---|---|
| 264 g; 2.06 mol; 1 eq. Mw: 128.13; GC (area) >99% | 1000 ml; 6.84 mol; 3 eq. Mw: 45.08; 33% in water |

The anhydride was obtained by Procedure F.
The amide acid was obtained according to Procedure D.
Crude product=368 g (red oil) (isomers 29/71)
Step 2
Raw Materials

| Amide acid | Methanol | Thionyl chloride |
|---|---|---|
| 236 g; 1.36 mol; 1 eq Mw: 173.21 | 2360 ml; Mw: 32.04 | 236 ml; 3.25 mol; 2.4 eq; Mw: 118.97; 99% |

The methyl ester dimethylamide was obtained according to Procedure E.
Crude product=300 g
Final product=171 g, Yield=68%
GC analysis (area)>99% (isomers 31/69)

Example 1.5

Preparation of isoamyl-OOC-$A_{MG}$-CONMe$_2$

The synthesis route was the following (only the majority species are represented):

A mixture known as crude "MGN" comprising 2-methyl-glutaronitrile (2-MGN) in the majority, ethylsuccinonitrile (ESN) and adiponitrile (ADN) was hydrolysed so as to obtain a mixture known as MGA: Mixture comprising 2-methylglutaric acid (86 mol %), ethylsuccinic acid (11 mol %) and adipic acid (3 mol %).

A conversion to anhydride was carried out according to Procedure F.

Next the following steps were carried out:
Step 1
Raw Materials

| Cyclic anhydride | DMA aq. |
|---|---|
| 780 g; 6.09 mol; 1 eq Mw: 128.13; GC (area) >99% | 2500 ml; 16.31 mol; 2.6 eq. Mw: 45.08; 33% in water |

The amide acid was obtained according to Procedure D.
Crude product=1120 g (yellow liquid) (isomers 29/71)
Step 2
Raw Materials

| Amide acid | 3-methyl-1-butanol | Thionyl chloride |
|---|---|---|
| 1510 g; 8.2 mol; 1 eq Mw: 173.21 | 2869 ml; 25.7 mol; 3.2 eq Mw: 88.15 | 1446 ml; 19.69 mol; 2.5 eq Mw: 118.97; 99% |

The ester dimethylamide was obtained according to Procedure E.
Crude product=300 g
Final product=1242 g (Boiling point ~132° C./70 Pa)
GC analysis (area)>96% (isomers 31/69)
Given below is the detail of the GC analysis.

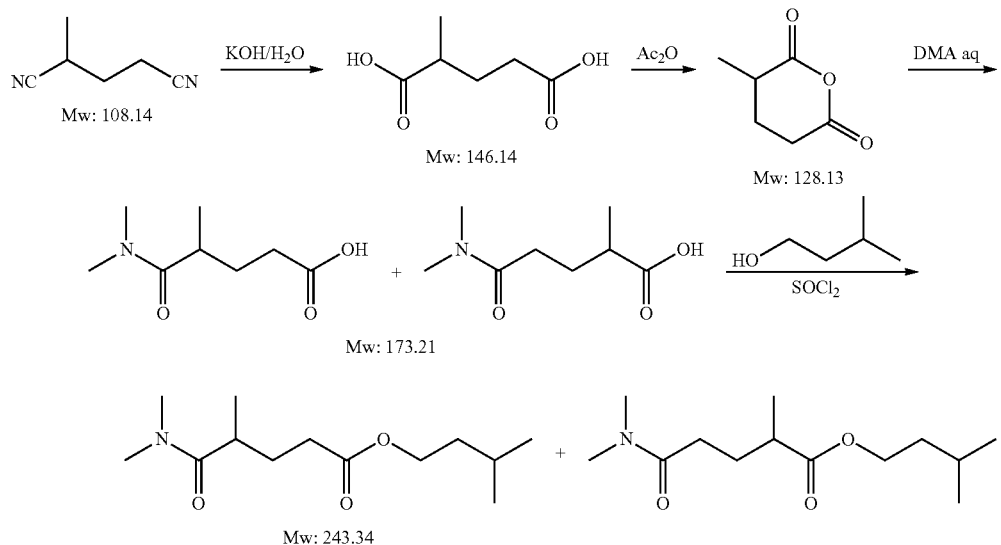

| Compound | GC (area) |
|---|---|
| 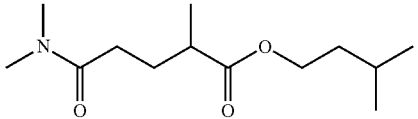 [SMILES: CC(C)CCOC(=O)C(C)CCC(=O)N(C)C] | 54.72% |
| 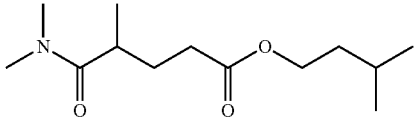 [SMILES: CC(C)CCOC(=O)CCC(C)C(=O)N(C)C] | 21.25% |
| 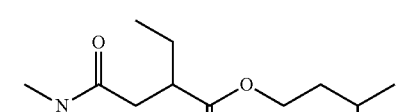 | 5.11% |
| 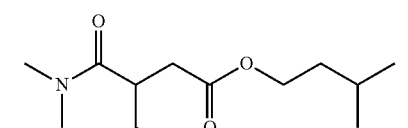 | 2.75% |
| 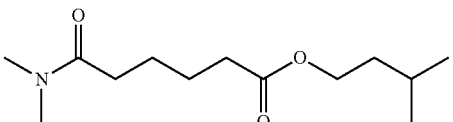 | 0.59% |
| Diester(s) | 14.97% |

Example 1.6

Preparation of cyclohexyl-OOC-A$_{MG}$-CONMe$_2$

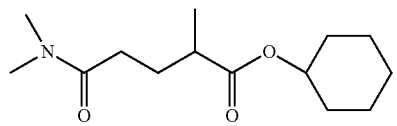 [SMILES: CC(CCC(=O)N(C)C)C(=O)OC1CCCCC1]

A mixture known as crude "MGN" comprising 2-methylglutaronitrile (2-MGN) in the majority, ethylsuccinonitrile (ESN) and adiponitrile (ADN) was hydrolysed so as to obtain a mixture known as MGA: Mixture comprising 2-methylglutaric acid (86 mol %), ethylsuccinic acid (11 mol %) and adipic acid (3 mol %).

A conversion to anhydride was carried out according to Procedure F.

Next the following steps were carried out:

Step 1
Raw Materials

| Cyclic anhydride | DMA aq. |
|---|---|
| 331 g; 2.58 mol; 1 eq<br>Mw: 128.13; GC (area) >99% | 1030 ml; 6.72 mol; 2.6 eq.<br>Mw: 45.08; 33% in water |

The amide acid was obtained according to Procedure D.
Crude product=440 g (yellow liquid) (isomers 29/71), >94.7% GC Step 2
Raw Materials

| Amide acid | Cyclohexanol | Thionyl chloride |
|---|---|---|
| 400 g; 2.31 mol; 1 eq<br>Mw: 173.21 | 289 g; 1.25 mol eq<br>Mw: 100 | 302 g; 2.54 mol; 1.1 eq<br>Mw: 118.97; 99% |

The ester dimethylamide was obtained according to Procedure E except that the amide acid was dissolved in dichloromethane before the reaction.

Final product=430 g (boiling point ~140-144° C./40 Pa), % Yield=73%

GC analysis (area)>97%

Given below is the detail from the GC analysis.

| Compound | GC (area) |
|---|---|
| 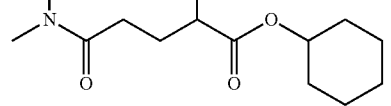 | 52.05% |
| 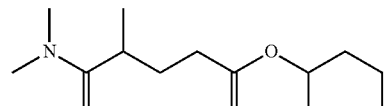 | 33.71% |
| 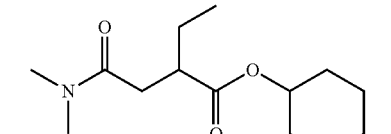 | 7.47% |
| 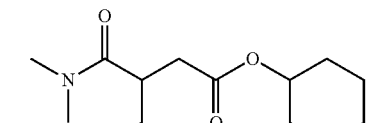 | 2.95% |
| 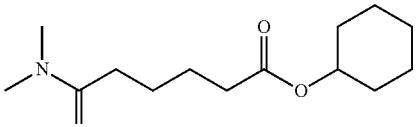 | 0.83% |
| 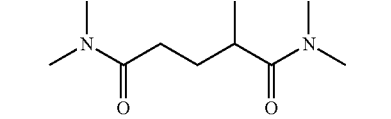 | 1.41% |
| 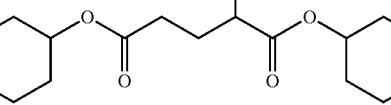 | 0.75% |

Example 1.7

Preparation of 2-ethylhexyl-OOC-$A_{MG}$-CONMe$_2$

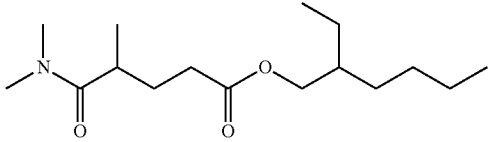 [SMILES: CCCCC(CC)COC(=O)CCC(C)C(=O)N(C)C]

A mixture known as crude "MGN" comprising 2-methylglutaronitrile (2-MGN) in the majority, ethylsuccinonitrile (ESN) and adiponitrile (ADN) was hydrolysed so as to obtain a mixture known as MGA: Mixture comprising 2-methylglutaric acid (86 mol %), ethylsuccinic acid (11 mol %) and adipic acid (3 mol %).

A conversion to anhydride was carried out according to Procedure F.

Next Procedure D was carried out.

Next the following steps were carried out:

Step 1
Raw Materials

| Amide acid | 2-Ethylhexanol | Thionyl chloride |
|---|---|---|
| 350 g; 2.02 mol; 1 eq Mw: 173.21 | 395 ml; 2.53 mol; 1.25 eq Mw: 130 | 160 ml; 2.22 mol; 1.1 eq Mw: 118.97; 99% |

The ester dimethylamide was obtained according to Procedure E except that the amide acid was dissolved in dichloromethane before the reaction.

Final product=308 g (boiling point ~148-150° C./80 Pa),
Yield=52%
GC analysis (area)>96%

The detail from the GC analysis is given below.

| Compound | GC (area) |
|---|---|
| | 58.68% |
| | 26.91% |
| | 7.82% |
| | 2.26% |
| | 0.37% |
| Diester(s) | 3.26% |

Example 1.8

Preparation of isoamyl-OOC-$A_{MG}$-CONEt$_2$

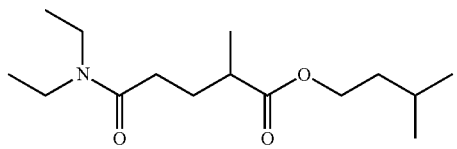 [SMILES: CCN(CC)C(=O)CCC(C)C(=O)OCCC(C)C]

A mixture known as crude "MGN" comprising 2-methylglutaronitrile (2-MGN) in the majority, ethylsuccinonitrile (ESN) and adiponitrile (ADN) was hydrolysed so as to obtain a mixture known as MGA: Mixture comprising 2-methylglutaric acid (86 mol %), ethylsuccinic acid (11 mol %) and adipic acid (3 mol %).

A conversion to anhydride was carried out according to Procedure F.

Next the following steps were carried out:

Step 1
Raw Materials

| Cyclic anhydride | DEA aq. |
|---|---|
| 420 g; 3.28 mol; 1 eq Mw: 128.13; GC (area) >99% | 880 ml; 8.53 mol; 2.6 eq. Mw: 73.1 |

The amide acid was obtained according to Procedure D.
Crude product=765 g (yellow liquid), >90% by GC Step 2
Raw Materials

| Amide acid | 3-methylbutan-1-ol | Thionyl chloride |
|---|---|---|
| 660 g; 3.3 mol; 1 eq Mw: 173.21 | 364 g; 1.25 mol eq Mw: 88.15 | 426 g; 3.6 mol; 1.1 eq Mw: 118.97; 99% |

The ester diethylamide was obtained according to Procedure E except that the amide acid was dissolved in dichloromethane before the reaction.

Final product=460 g (boiling point ~150-158° C./200 Pa), % Yield=64%

GC analysis (area)>98%

Given below is the detail from the GC analysis.

| Compound | GC (area) |
|---|---|
| 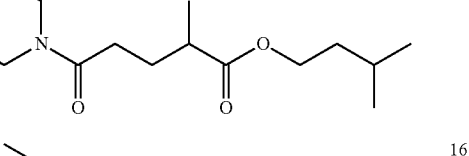 | 70.25% |
| 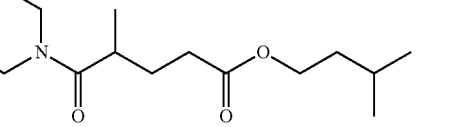 | 16.07% |
| 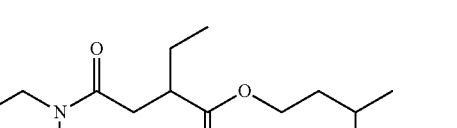 | 8.49% |
| 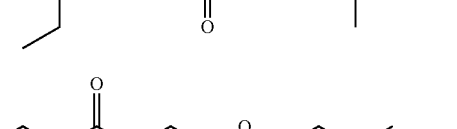 | 4.45% |
| 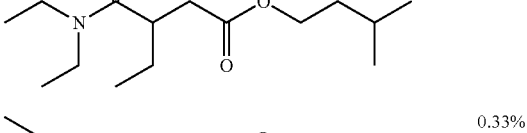 | 0.33% |
| Di-amide | 0.41% |
| Di-ester isomer | N.D |
| Total GC area % | 100% |

Example 1.9

Preparation of cyclohexyl-OOC-$A_{MG}$-CONEt$_2$

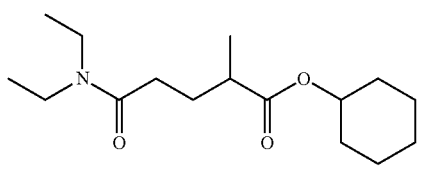 [SMILES: CCN(CC)C(=O)CCC(C)C(=O)OC1CCCCC1]

A mixture known as crude "MGN" comprising 2-methylglutaronitrile (2-MGN) in the majority, ethylsuccinonitrile (ESN) and adiponitrile (ADN) was hydrolysed so as to obtain a mixture known as MGA: Mixture comprising 2-methylglutaric acid (86 mol %), ethylsuccinic acid (11 mol %) and adipic acid (3 mol %).

A conversion to anhydride was carried out according to Procedure F.

Next Procedure D was carried out.

Next the following steps were carried out:

Raw Materials

| Amide acid | Cyclohexanol | Thionyl chloride |
|---|---|---|
| 402 g; 2.0 mol; 1 eq | 240 g; 2.4 mol; 1.2 eq | 160 ml; 2.2 mol; 1.1 eq |
| Mw: 173.21 | Mw: 100 | Mw: 118.97; 99% |

The ester diethylamide was obtained according to Procedure E except that the amide acid was dissolved in dichloromethane before the reaction.

Final product=418 g (boiling point ~142-146° C./80 Pa), % Yield=73.7%

GC analysis (area)>98%

The detail from the GC analysis is given below.

| Compound | GC (area) |
|---|---|
| Various | 0.53% |
| Diester(s) | 0.04% |
| 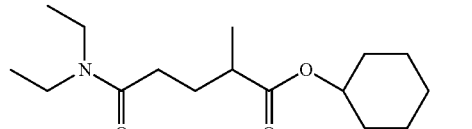 | 70.65% |
| 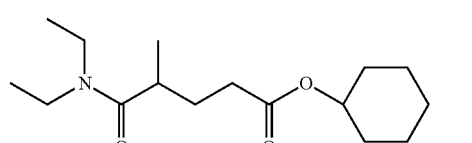 | 17.22% |
| 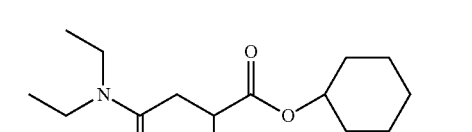 | 7.03% |
| 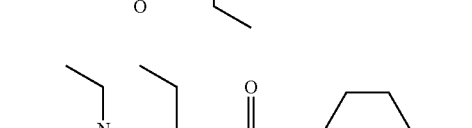 | 3.52% |
| 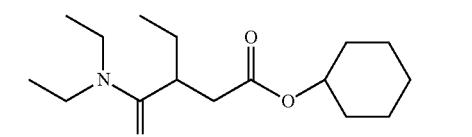 | 0.74% |
| Diamides | 0.26% |
| Total GC area % | 100% |

Example 1.10

Preparation of n-butyl-OOC-A$_{MG}$-CONEt$_2$

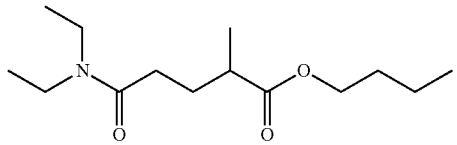 [SMILES: CCCCOC(=O)C(C)CCC(=O)N(CC)CC]

A mixture known as crude "MGN" comprising 2-methylglutaronitrile (2-MGN) in the majority, ethylsuccinonitrile (ESN) and adiponitrile (ADN) was hydrolysed so as to obtain a mixture known as MGA: Mixture comprising 2-methylglutaric acid (86 mol %), ethylsuccinic acid (11 mol %) and adipic acid (3 mol %).

A conversion to anhydride was carried out according to Procedure F.

Next Procedure D was carried out.

Next the following steps were carried out:

Raw Materials

| Amide acid | n-butanol | Thionyl chloride |
|---|---|---|
| 500 g, 2.335 mol, 1 eq Mw: 173.21 | 270 ml, 2.92 mol, 1.25 eq Mw: 74 | 187 ml, 2.57 mol, 1.1 eq Mw: 118.97, 99% |

The ester diethylamide was obtained according to Procedure E except that the amide acid was dissolved in dichloromethane before the reaction.

Final product=443 g (boiling point ~144° C./80 Pa), % Yield=72.8%

GC analysis (area)>98%

The detail from the GC analysis is given below.

| Compound | GC (area) |
|---|---|
| Various | 0.22% |
| Diester(s) | 0.36% |
| 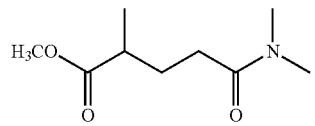 | 71.07% |
| (structure) | 17.98% |
| (structure) | 6.88% |
| (structure) | 2.61% |
| (structure) | 0.76% |
| Diamide(s) | 0.12% |
| Total GC area % | 100% |

Example 1.11

Preparation of a Mixture Comprising -MeOOC-A$_{MG}$-CONMe$_2$ (Main Compound) and MeOOC-A$_{ES}$-CONMe$_2$ The formula of the main compound is (structure: H$_3$CO-C(=O)-CH(CH$_3$)-CH$_2$-CH$_2$-C(=O)-N(CH$_3$)$_2$)

Raw Materials

| Methanol | Dimethylamine | Sodium methylate in methanol | Methyl diesters | Sulphuric acid |
|---|---|---|---|---|
| 800 kg | 1300 kg 28.89 kmol | 240 kg (60 kg MeONa) 1.11 kmol | 4080 kg 23.45 kmol | 55 kg 0.55 kmol |

A transamidification reaction was carried out on a mixture of methyl diesters comprising dimethyl 2-methylglutarate (85% by weight), ethylsuccinate (12% by weight) and adipate (3% by weight).

Added to a mixture of anhydrous methanol and dimethylamine gas cooled to 5° C.+/−5° C. were sodium methylate in a methanolic solution, then slowly, over 4 hours, the mixture of methyl diesters was added while maintaining the temperature at 10° C.+/−5° C.

The reaction was completed in 8 hours at 15° C.+/−5° C.

The excess of dimethylamine was then removed by distillation up to a temperature of 25° C.+/−5° C. and a vacuum of 200 mbar while carrying over methanol. The condensed mixture of dimethylamine in solution in methanol was recycled in the following charge. Catalytic sodium methylate was neutralized with concentrated sulphuric acid or with ion exchange resins (sulphonic resins of Amberlist or Amberlit type).

The sodium sulphate or the resin was removed from the medium by filtration and rinsed with fresh methanol.

The methanol was then removed by distillation under vacuum (up to 120° C. and 10 mbar) carrying over the methyl diesters that had not reacted (representing 1% of the yield); the mixture of methanol and of methyl diesters was recycled into the production of the methyl diesters.

The product was then distilled under a maximum temperature in the reboiler of 140° C. and a vacuum of 5 mbar; recovered therefrom were 4050 kg, representing a yield of 92.3%.

The distillation residue still contained 280 kg of product (yield of 6.3%); it was recycled into the distillation of the following operation.

The typical analysis of the distilled product was the following:

Appearance: clear colourless to light yellow liquid.
Coloration: 100 APHA max
GC analysis:
Sum of the esteramide isomers: 96% min
Sum of the diamide isomers: 3+/−1%
Sum of the unreacted diester isomers: 0.5% max
Methanol: 500 ppm max
Water content: 100 ppm max
Acid index: 0.8 mg KOH/g of product max Example 1.12

Preparation of t-butyl-OOC-A$_{MG}$-CONMe$_2$

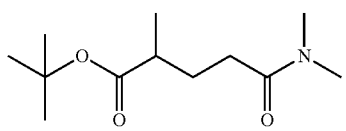 [SMILES: CC(CCC(=O)N(C)C)C(=O)OC(C)(C)C]

The synthesis route was the following (only the majority species are represented):

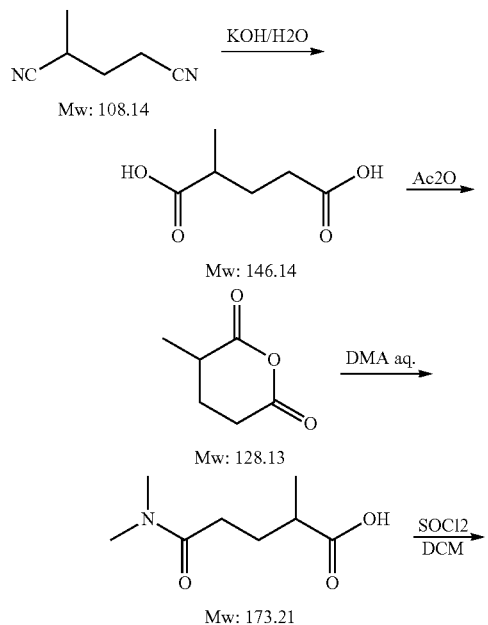

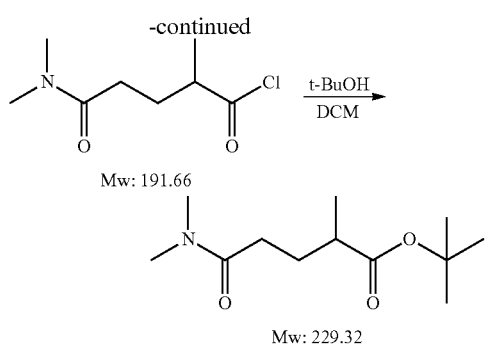

A mixture known as crude "MGN" comprising 2-methyl-glutaronitrile (2-MGN) in the majority, ethylsuccinonitrile (ESN) and adiponitrile (ADN) was hydrolysed so as to obtain a mixture known as MGA: Mixture comprising 2-methylglutaric acid (86 mol %), ethylsuccinic acid (11 mol %) and adipic acid (3 mol %).

A conversion to anhydride was carried out according to Procedure F.

Next the following steps were carried out:
Step 1
Raw Materials

| Cyclic anhydride | DMA aq. |
|---|---|
| 370 g; 2.89 mol; 1 eq. Mw: 128.13; GC (area) >99% | 1152 ml; 7.51 mol; 2.6 eq. Mw: 45.08; 33% in water |

The amide acid was obtained according to Procedure D.
Crude product=550 g (pale yellow liquid)
Step 2
Raw Materials

| Amide acid | Dichloromethane | Thionyl chloride |
|---|---|---|
| 592 g; 3.42 mol; 1 eq Mw: 173.21 | 1000 ml | 274 ml; 3.76 mol; 1.1 eq; Mw: 118.97; 99% |

The amide acid was mixed with dichloromethane then cooled to around 4° C. The thionyl chloride was slowly charged over around 1.5 h while controlling the temperature below 25° C. The reaction mixture was stirred at ambient temperature for 10 h. The volatile species were withdrawn to obtain the crude product.
Crude product=687 g (dark liquid).
Step 3
Raw Materials

| Crude product from Step 2 | Dichloromethane | tert-butanol |
|---|---|---|
| 305 g; 1.52 mol; 1 eq Mw: 191.66 | 300 ml + 300 ml | 72 ml; 0.77 mol; 2 eq; Mw: 74; 99% |

The dichloromethane was mixed with the tert-butanol and cooled to 4° C. The crude product from step 2, diluted in dichloromethane, was then added slowly over around 1.5 h while controlling the temperature below 10° C. The volatiles were drawn off using a rotary evaporator. The reaction crude was treated with 1500 g of sodium hydrogencarbonate then filtered. The cake was washed with 1500 ml of dichloromethane and the filtrate was dried over sodium sulphate. After evaporation of the solvent, the crude product was obtained. The latter was purified by distillation (120° C./250 Pa).

Crude product=301 g
Final product=150 g
GC analysis (area)>98% (isomers 8/92)

Example 1.13

Preparation of Et-butyl-OOC-$A_{MG}$-CONMe$_2$

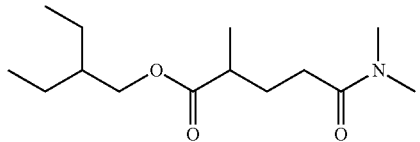 [SMILES: CCC(CC)COC(=O)C(C)CCC(=O)N(C)C]

The synthesis route was the following (only the majority species are represented):

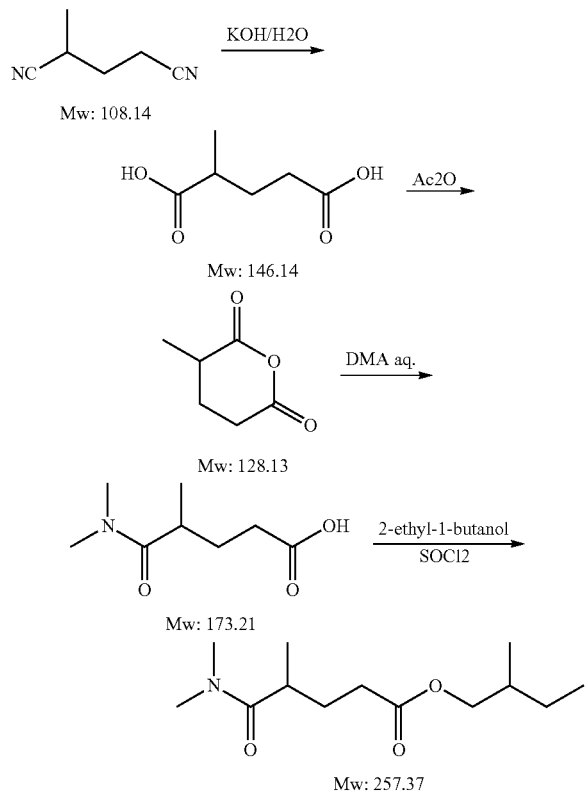

A mixture known as crude "MGN" comprising 2-methylglutaronitrile (2-MGN) in the majority, ethylsuccinonitrile (ESN) and adiponitrile (ADN) was hydrolysed so as to obtain a mixture known as MGA: Mixture comprising 2-methylglutaric acid (86 mol %), ethylsuccinic acid (11 mol %) and adipic acid (3 mol %).

A conversion to anhydride was carried out according to Procedure F.

Next the following steps were carried out:
Step 1
Raw Materials

| Cyclic anhydride | DMA aq. |
| --- | --- |
| 397 g; 3.1 mol; 1 eq. Mw: 128.13; GC (area) >99% | 1237 ml; 8.06 mol; 2.6 eq. Mw: 45.08; 33% in water |

The amide acid was obtained according to Procedure D.
Crude product=599 g (pale yellow liquid)
Step 2
Raw Materials

| Amide acid | 2-ethyl butanol | Dichloromethane | Thionyl chloride |
| --- | --- | --- | --- |
| 599 g; 3.46 mol; 1 eq Mw: 173.21 | 721 g; 6.92 mol; Mw: 32.04 | 550 ml | 253 ml; 3.49 mol; 1.01 eq; Mw: 118.97; 99% |

The methyl ester dimethylamide was obtained according to Procedure E.
Crude product=772 g
Final product=420 g, Yield=51.5%
GC analysis (area)>98% (isomers 8/92)

Examples 2.1 Onwards

Uses as Solvents—Phytosanitary Formulations

By mixing of the ingredients, formulations of various phytosanitary active agents of emulsifiable concentrate (EC) type were prepared.

The formulations comprise:
the active agent, in an amount by weight (of active ingredient) indicated in the table below;
10% by weight of surfactant Alkamuls® RC, sold by Rhodia; and
as solvent, the rest of the compound or composition of matter of the examples.

Example 2.1.1 is a comparative example where used as a solvent is the product Rhodiasolv® ADMA10, Rhodia (Asia-Pacific zone): alkyldimethylamide solvent.

The following tests were carried out:
Visual observation at 25° C.—the appearance of the formulation was noted and possibly the presence of crystals was spotted.

Visual observation at 0° C.—the formulation was placed at 0° C. for 7 days and the appearance of the formulation was noted and possibly the presence of crystals was spotted (CIPAC MT39 test)

Visual observation at 0° C. with nucleation: a crystal of the active ingredient was introduced into the formulation that had spent 7 days at 0° C. for nucleation, and the formulation was again placed at 0° C. for 7 days. The appearance of the formulation was noted and possibly the presence of crystals was spotted.

| Example | Solvent | Active agent | Appearance at 25° C. | Appearance at 0° C. | Appearance at 0° C. with nucleation |
|---|---|---|---|---|---|
| 2.1.1C | Rhodiasolv ® ADMA 10 | Oxyfluorfen - 22% | Clear | Clear | Crystals |
| 2.1.2C | Rhodiasolv ® ADMA 10 | Propuxur - 20% | Clear | Clear | Crystals |
| 2.1.3C | Rhodiasolv ® ADMA 10 | Dimethoate - 40% | Cloudy | Cloudy | Crystals |
| 2.1.4C | Rhodiasolv ® ADMA 10 | Alachlor - 48% | Clear | Crystals | Crystals |
| 2.1.10C | Rhodiasolv ® ADMA 10 | Difenconazole - 25% | Clear | Clear | Clear |
| 2.1.11C | Rhodiasolv ® ADMA 10 | Triadimenol - 23% | Clear | Clear | Crystals |
| 2.2.2 | Example 1.1 | Propuxur - 20% | Clear | Clear | Clear |
| 2.2.3 | Example 1.1 | Dimethoate - 40% | Clear | Clear | Clear |
| 2.2.4 | Example 1.1 | Alachlor - 48% | Clear | Clear | Crystals |
| 2.2.6 | Example 1.1 | Fastac - 10% | Clear | Clear | Clear |
| 2.2.7 | Example 1.1 | Phenmedipham - 16% | Clear | Clear | Clear |
| 2.2.8 | Example 1.1 | Propanil - 36% | Clear | Clear | Clear |
| 2.2.9 | Example 1.1 | Tebuconazole - 25% | Clear | Clear | Clear |
| 2.2.10 | Example 1.1 | Difenconazole - 25% | Clear | Clear | Clear |
| 2.3.2 | Example 1.2 | Propuxur - 20% | Clear | Clear | Clear |
| 2.3.3 | Example 1.2 | Propuxur - 20% | Clear | Clear | Clear |
| 2.3.5 | Example 1.2 | Chlorpyrifos - 40% | Clear | Clear | Clear |
| 2.3.6 | Example 1.2 | Fastac - 10% | Clear | Clear | Clear |
| 2.3.7 | Example 1.2 | Phenmedipham - 16% | Clear | Clear | Clear |
| 2.3.9 | Example 1.2 | Tebuconazole - 25% | Clear | Clear | Clear |
| 2.3.10 | Example 1.2 | Difenconazole - 25% | Clear | Clear | Clear |
| 2.4.1 | Example 1.3 | Oxyfluorfen - 22% | Clear | Clear | Clear |
| 2.4.2 | Example 1.3 | Propuxur - 20% | Clear | Clear | Clear |
| 2.4.4 | Example 1.3 | Alachlor - 48% | Clear | Clear | Crystals |
| 2.4.5 | Example 1.3 | Chlorpyrifos - 40% | Clear | Clear | Clear |
| 2.4.6 | Example 1.3 | Fastac - 10% | Clear | Clear | Clear |
| 2.4.7 | Example 1.3 | Phenmedipham - 16% | Clear | Clear | Clear |
| 2.4.8 | Example 1.3 | Propanil - 36% | Clear | Clear | Clear |
| 2.4.9 | Example 1.3 | Tebuconazole - 25% | Clear | Clear | Clear |
| 2.5.4 | Example 1.5 | Alachlor - 48% | Clear | Clear | Crystals |
| 2.5.5 | Example 1.5 | Chlorpyrifos - 40% | Clear | Clear | Clear |
| 2.5.6 | Example 1.5 | Fastac - 10% | Clear | Clear | Clear |
| 2.5.7 | Example 1.5 | Phenmedipham - 16% | Clear | Clear | Clear |
| 2.5.8 | Example 1.5 | Propanil - 36% | Clear | Clear | Clear |
| 2.5.9 | Example 1.5 | Tebuconazole - 25% | Clear | Clear | Clear |
| 2.6.4 | Example 1.6 | Alachlor - 48% | Clear | Clear | Crystals |
| 2.6.8 | Example 1.6 | Propanil - 36% | Clear | Clear | Clear |
| 2.6.11 | Example 1.6 | Triadimenol - 23% | Clear | Clear | Clear |
| 2.7.4 | Example 1.7 | Alachlor - 48% | Clear | Clear | Crystals |
| 2.7.8 | Example 1.7 | Propanil - 36% | Clear | Clear | Clear |
| 2.8.4 | Example 1.8 | Alachlor - 48% | Clear | Clear | Crystals |
| 2.8.8 | Example 1.8 | Propanil - 36% | Clear | Clear | Clear |
| 2.9.4 | Example 1.9 | Alachlor - 48% | Clear | Clear | Crystals |
| 2.9.8 | Example 1.9 | Propanil - 36% | Clear | Clear | Clear |
| 2.9.9 | Example 1.9 | Tebuconazole - 25% | Clear | Clear | Clear |
| 2.10.4 | Example 1.10 | Alachlor - 48% | Clear | Clear | Crystals |
| 2.10.8 | Example 1.10 | Propanil - 36% | Clear | Clear | Clear |
| 2.10.10 | Example 1.10 | Difenconazole - 25% | Clear | Clear | Clear |
| 2.11.1 | Example 1.11 | Oxyfluorfen - 22% | Clear | Clear | Clear |
| 2.11.3 | Example 1.11 | Dimethoate - 40% | Clear | Clear | Crystals |
| 2.11.4 | Example 1.11 | Propuxur - 20% | Clear | Clear | Clear |
| 2.11.5 | Example 1.11 | Chlorpyrifos - 40% | Clear | Clear | Clear |
| 2.11.7 | Example 1.11 | Phenmedipham - 16% | Clear | Clear | Clear |
| 2.11.8 | Example 1.11 | Propanil - 36% | Clear | Clear | Clear |
| 2.11.9 | Example 1.11 | Tebuconazole - 25% | Clear | Clear | Clear |
| 2.11.10 | Example 1.11 | Difenconazole - 25% | Clear | Clear | Clear |
| 2.12.4 | Example 1.12 | Alachlor - 48% | Clear | Clear | Crystals |
| 2.12.5 | Example 1.12 | Chlorpyrifos - 40% | Clear | Clear | Clear |
| 2.12.7 | Example 1.12 | Phenmedipham - 16% | Clear | Clear | Clear |
| 2.12.8 | Example 1.12 | Propanil - 36% | Clear | Clear | Clear |
| 2.12.9 | Example 1.12 | Tebuconazole - 25% | Clear | Clear | Clear |
| 2.12.11 | Example 1.12 | Triadimenol - 23% | Clear | Clear | Crystals |
| 2.13.3 | Example 1.13 | Dimethoate - 40% | Clear | Clear | Crystals |
| 2.13.4 | Example 1.13 | Alachlor - 48% | Clear | Clear | Crystals |

The invention claimed is:

1. A composition comprising at least one esteramide compound having the formula (I) below:

R$^1$OOC-A-CONR$^2$R$^3$ (I)

in which:

R$^1$ is a radical selected from among saturated or unsaturated, linear or branched, optionally cyclic, optionally aromatic hydrocarbon-based radicals having an average number of carbon atoms ranging from 1 to 36;

R$^2$ and R$^3$, which may be identical or different, are each radicals selected from among saturated or unsaturated, linear or branched, optionally cyclic, optionally aromatic, optionally substituted hydrocarbon-based radicals having an average number of carbon atoms ranging from 1 to 36, with the proviso that R$^2$ and R$^3$ may optionally together form a ring member that is optionally substituted and/or that optionally contains a heteroatom; and A is a branched divalent alkyl radical having an average number of carbon atoms ranging from 2 to 12, wherein said composition is formulated as a phytosanitary cleaning, degreasing, stripping, lubricating, coating, or pigment/ink composition and where said at least one esteramide compound having the formula (I) solubilizes and/or coalesces other ingredients in said composition.

2. The composition as defined by claim 1, where in formula (I), $R^2$ and $R^3$ are ethyl radicals.

3. The composition as defined by claim 1, where in formula (I), $R^1$, $R^2$ and $R^3$, which may be identical or different, are each radicals selected from among $C_1$-$C_{12}$ alkyl, aryl, alkaryl or arylalkyl radicals or the phenyl radical, $R^2$ and/or $R^3$ optionally being substituted.

4. The composition as defined by claim 1, where in formula (I), $R^1$ is selected from among methyl, ethyl, propyl, isopropyl, n-butyl, isobutyl, n-pentyl, isopentyl, isoamyl, n-hexyl, cyclohexyl, 2-ethylbutyl, n-octyl, isooctyl, 2-ethylhexyl, and tridecyl radicals.

5. The composition as defined by claim 1, where in formula (I), $R^2$ and $R^3$, which may be identical or different, are each selected from the group consisting of methyl, ethyl, n-propyl, isopropyl, n-butyl, isobutyl, n-pentyl, amyl, isoamyl, hexyl, cyclohexyl, hydroxyethyl, morpholine, piperazine and piperidine groups.

6. The composition as defined by claim 1, where in formula (I), A is a divalent branched alkylene radical having one of the following formulae (IIa), (IIb), (IIc), (IIIa) and (IIIb), or a mixture of at least two radicals selected from the radicals of formulae (IIa), (IIb) and (IIc) or from the radicals of formulae (IIIa) and (IIIb), or a mixture of at least two radicals, one selected from the groups of formulae (IIa), (IIb) and (IIc) and the others selected from the radicals of formulae (IIIa) and (IIIb):

$$—(CHR^7)_y—(CHR^6)_x—(CHR^7)_z—CH_2—CH_2— \quad (IIa)$$

$$—CH_2—CH_2—(CHR^7)_z—(CHR^6)_x—(CHR^7)_y— \quad (IIb)$$

$$—(CHR^7)_z—CH_2—(CHR^6)_x—CH_2—(CHR^7)_y— \quad (IIc)$$

$$—(CHR^7)_y—(CHR^6)_x—(CHR^7)_z—CH_2— \quad (IIIa)$$

$$—CH_2—(CHR^7)_z—(CHR^6)_x—(CHR^7)_y— \quad (IIIb)$$

wherein:
x is an integer greater than 0;
y is an average integer greater than or equal to 0;
z is an average integer greater than or equal to 0;
the radicals $R^6$, which may be identical or different, are each a $C_1$-$C_6$ alkyl radical; and
the radicals $R^7$, which may be identical or different, are each a hydrogen atom or a $C_1$-$C_6$ alkyl radical.

7. The composition as defined by claim 6, wherein the formula (IIa) and/or in the formula (IIb) x=1; y=z=0; $R^6$=methyl; and/or in the formula (IIIa) and/or in the formula (IIIb) x=1; y=z=0; $R^6$=ethyl.

8. The composition as defined by claim 6, wherein said at least one esteramide compound is selected from the group consisting of following compounds, and mixtures thereof:

MeOOC-A$_{MG}$-CONMe$_2$;

MeOOC-A$_{ES}$-CONMe$_2$;

PeOOC-A$_{MG}$-CONMe$_2$;

PeOOC-A$_{ES}$-CONMe$_2$;

CycloOOC-A$_{MG}$-CONMe$_2$;

CycloOOC-A$_{ES}$-CONMe$_2$;

EhOOC-A$_{MG}$-CONMe$_2$;

EhOOC-A$_{ES}$-CONMe$_2$;

PeOOC-A$_{MG}$-CONEt$_2$;

PeOOC-A$_{ES}$-CONEt$_2$;

CycloOOC-A$_{MG}$-CONEt$_2$;

CycloOC-A$_{ES}$-CONEt$_2$;

BuOOC-A$_{MG}$-CONEt$_2$;

BuOC-A$_{ES}$-CONEt$_2$;

BuOOC-A$_{MG}$-CONMe$_2$;

BuOOC-A$_{ES}$-CONMe$_2$;

EtBuOOC-A$_{MG}$-CONMe$_2$; and

EtBuOOC-A$_{ES}$-CONMe$_2$;

wherein:
A$_{MG}$ is an MG$_a$ radical of formula —CH(CH$_3$)—CH$_2$—CH$_2$—, or MG$_b$ radical of formula —CH$_2$—CH$_2$—CH(CH$_3$)— or a mixture of MG$_a$ and MG$_b$ radicals;
A$_{ES}$ is an ES$_a$ radical of formula —CH(C$_2$H$_5$)—CH$_2$—, or ES$_b$ radical of formula —CH$_2$—CH(C$_2$H$_5$)— or a mixture of ES$_a$ and ES$_b$ radicals;
Pe is a pentyl radical;
Cyclo is a cyclohexyl radical;
Eh is a 2-ethylhexyl radical;
Bu is a butyl radical; and
EtBu is an ethylbutyl radical.

9. The composition as defined by claim 1, wherein said at least one esteramide compound is different from the following compounds:

MeOOC—CHEt-CH$_2$—CONMe$_2$; and

MeOOC—CH$_2$—CH(CH$_3$)—CH$_2$—CONMe$_2$.

10. The composition as defined by claim 1, wherein said at least one esteramide compound is different from the following compounds thereof:

MeOOC—CHEt-CH$_2$—CONMe$_2$;

MeOOC—CH$_2$—CH(CH$_3$)—CH$_2$—CONMe$_2$;

PhOOC—CH(CH$_3$)—CH$_2$—CONEt$_2$;

EtOOC—CH(CH$_3$)—CH$_2$—CONEt$_2$;

MeOOC—CH(CH$_3$)—CH$_2$—CONEt$_2$;

Me-CH(OMe)-OOC—CH(CH$_3$)—CH$_2$—CONEt$_2$;

Cyclohexyl-OOC—CH(CH$_3$)—CH$_2$—CONEt$_2$;

Ph-CH$_2$OOC—CH(CH$_3$)—CH$_2$—CONEt$_2$;

p-cresyl-OOC—CH(CH$_3$)—CH$_2$—CONEt$_2$;

EtOOC—CHEt-CH$_2$—CONEt$_2$;

EtOOC—CH(CH₃)—CH₂—CH₂—CONEt₂;

EtOOC—CH₂—CH₂—CH₂—CH₂—CONEt₂; and

MeOOC—CH₂—CH(CH₃)—CH₂—CONH(n-butyl).

11. The composition as defined by claim 1, wherein said at least one esteramide compound has a melting point that is less than or equal to 20° C.

12. At least one esteramide compound having the formula (I) below:

R¹OOC-A-CONR²R³                                   (I)

wherein:
R¹ is a radical selected from among saturated or unsaturated, linear or branched, optionally cyclic, optionally aromatic hydrocarbon-based radicals having an average number of carbon atoms ranging from 1 to 36;
R² and R³, which may be identical or different, are each radicals selected from among saturated or unsaturated, linear or branched, optionally cyclic, optionally aromatic, optionally substituted hydrocarbon-based radicals having an average number of carbon atoms ranging from 1 to 36, with the proviso that R² and R³ may optionally together form a ring member, that is optionally substituted and/or that optionally contains a heteroatom; and
A is a branched divalent alkyl radical having an average number of carbon atoms ranging from 2 to 12, other than the following compounds:

MeOOC—CHEt-CH₂—CONMe₂;

MeOOC—CH₂—CH(CH₃)—CH₂—CONMe₂;

PhOOC—CH(CH₃)—CH₂—CON Et₂;

EtOOC—CH(CH₃)—CH₂—CONEt₂;

MeOOC—CH(CH₃)—CH₂—CONEt₂;

Me-CH(OMe)-OOC—CH(CH₃)—CH₂—CONEt₂;

Cyclohexyl-OOC—CH(CH₃)—CH₂—CONEt₂;

Ph-CH₂OOC—CH(CH₃)—CH₂—CONEt₂;

p-cresyl-OOC—CH(CH₃)—CH₂—CONEt₂;

EtOOC—CHEt-CH₂—CONEt₂,

EtOOC—CH(CH₃)—CH₂—CH₂—CONEt₂;

MeOOC—CH₂—CH(CH₃)—CH₂—CONH(n-butyl).

13. A process for preparing an esteramide compound as defined in claim 12, comprising reacting an anhydride of formula (I') with an alcohol of formula R¹—OH and/or an amine of formula HNR²R³:

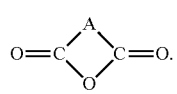
                                (I')

14. The process as defined by claim 13, wherein the anhydride is prepared during a prior step a) of cyclization of a diacid of formula HOOC-A-COOH.

15. The process as defined by claim 13, comprising one of the following reaction sequences 1) or 2):

Sequence 1):
Step 1b) the anhydride of formula (I') is reacted with an alcohol of formula R¹—OH, so as to obtain an ester acid compound of formula (I"):

R¹—OOC-A-COOH                              (I");

Step 1c) the compound of formula (I") is converted to a compound of formula (I) using an amine of formula HNR²R³;

Sequence 2):
Step 2b) the anhydride of formula (I') is reacted with an amine of formula HNR²R³ to obtain an amide acid compound of formula (II"):

HOOC-A-CONR²R³                              (II");

Step 2c) the compound of formula (II") is converted to a compound of formula (I) using an alcohol of formula R¹—OH.

16. The process as defined by claim 15, wherein step 1c) comprises the following steps:
1c1) the compound of formula (I") is converted to an acyl chloride of formula (I'") below:

R¹—OOC-A-COCl                              (I'");

1c2) the compound of formula (III'") is reacted with the amine of formula NR³R⁴ to obtain the compound of formula (I).

17. The process as defined by claim 15, wherein step 2c) is carried out in the presence of thionyl chloride.

18. A process for preparing an esteramide compound as defined in claim 12, comprising reacting as diester of formula R¹OOC-A-COOR¹ with an amine of formula HNR²R³, then optionally a reaction with an alcohol of formula R¹'—OH, wherein R¹' is a radical selected from among the R¹ radicals, but different from the R¹ radical of the diester.

19. At lease one esteramide compound as defined by claim 12, wherein R¹, R² and R³, which may be identical or different, are radicals selected from among C₁-C₁₂ alkyl, aryl, alkaryl or arylalkyl radicals or the phenyl radical, R² and/or R³ optionally being substituted.

20. At least one esteramide compound as defined by claim 12, wherein R¹ is selected from among methyl, ethyl, propyl, isopropyl, n-butyl, isobutyl, n-pentyl, isopentyl, isoamyl, n-hexyl, cyclohexyl, 2-ethylbutyl, n-octyl, isooctyl, 2-ethylhexyl, and tridecyl radicals.

21. At least one esteramide compound as defined by claim 12, wherein R² and R³, which may be identical or different, are each selected from among methyl, ethyl, propyl (n-propyl), isopropyl, n-butyl, isobutyl, n-pentyl, amyl, isoamyl, hexyl, cyclohexyl, hydroxyethyl, morpholine, piperazine and piperidine radicals.

22. At least one esteramide compound as defined by claim 12, wherein A is a divalent branched alkylene radical having one of the following formulae (IIa), (IIb), (IIc), (IIIa) and (IIIb), or a mixture of at least two radicals selected from among the radicals of formulae (IIa), (IIb) and (IIc) or from the radicals of formulae (IIIa) and (IIIb), or a mixture of at least two radicals, one selected from the radicals of formulae (IIa), (IIb) and (IIc) and the others selected from the radicals of formulae (IIIa) and (IIIb):

—(CHR⁷)ᵧ(CHR⁶)ₓ—(CHR⁷)_z—CH₂—CH₂—     (IIa)

—CH₂—CH₂—(CHR⁷)_z—(CHR⁶)ₓ—(CHR⁷)ᵧ     (IIb)

—(CHR⁷)_z—CH₂—(CHR⁶)ₓ—CH₂—(CHR⁷)ᵧ—     (IIc)

—(CHR⁷)ᵧ(CHR⁶)ₓ—(CHR⁷)_z—CH₂—     (IIIa)

—CH₂—(CHR⁷)_z—(CHR⁶)ₓ—(CHR⁷)ᵧ—     (IIIb)

wherein:
x is an integer greater than 0;
y is an average integer greater than or equal to 0;
z is an average integer greater than or equal to 0;
the radicals $R^6$, which may be identical or different, are each a $C_1$-$C_6$ alkyl radical; and
the radicals $R^7$, which may be identical or different, are each a hydrogen atom or a $C_1$-$C_6$ alkyl radical.

23. At least one esteramide compound as defined by claim 22, wherein formula (IIa) and/or in the formula (IIb) x=1; y=z=0; $R^6$=methyl; and/or in the formula (IIIa) and/or in the formula (IIIb) x=1; y=z=0; $R^6$=ethyl.

24. At least one esteramide compound as defined by claim 22, selected from among the following compounds, and mixtures thereof:

MeOOC-$A_{MG}$-CONMe$_2$;

MeOOC-$A_{ES}$-CONMe$_2$;

PeOOC-$A_{MG}$-CONMe$_2$;

PeOOC-$A_{ES}$-CONMe$_2$;

CycloOOC-$A_{MG}$-CONMe$_2$;

CycloOC-$A_{ES}$-CONMe$_2$;

EhOOC-$A_{MG}$-CONMe$_2$;

EhOOC-$A_{ES}$-CONMe$_2$;

PeOOC-$A_{MG}$-CONEt$_2$;

PeOOC-$A_{ES}$-CONEt$_2$;

CycloOOC-$A_{MG}$-CONEt$_2$;

CycloOC-$A_{ES}$-CONEt$_2$;

BuOOC-$A_{MG}$-CONEt$_2$;

BuOC-$A_{ES}$-CON Et$_2$;

BuOOC-$A_{MG}$-CONMe$_2$;

BuOOC-$A_{ES}$-CONMe$_2$;

EtBuOOC-$A_{MG}$-CONMe$_2$;

EtBuOOC-$A_{ES}$-CONMe$_2$;

n-HeOOC-$A_{MG}$-CONMe$_2$; and n-HeOOC-$A_{ES}$-CONMe$_2$;

wherein:
$A_{MG}$ is an MG$_a$ radical of formula —CH(CH$_3$)—CH$_2$—CH$_2$—, or MG$_b$ radical of formula —CH$_2$—CH$_2$—CH(CH$_3$)— or a mixture of MG$_a$ and MG$_b$ radicals;
$A_{ES}$ is an ES$_a$ radical of formula —CH(C$_2$H$_5$)—CH$_2$—, or ES$_b$ radical of formula —CH$_2$—CH(C$_2$H$_5$)— or a mixture of ES$_a$ and ES$_b$ radicals;
Pe is a pentyl radical;
Cyclo is a cyclohexyl radical;
Eh is a 2-ethylhexyl radical;
Bu is a butyl radical;
EtBu is an ethylbutyl radical; and
n-He is an n-hexyl radical.

25. A composition comprising:
(a) an active substance selected from the group consisting of an insecticide, a herbicide, a fungicide, an acaricide and a rodeticide;
(b) at least one esteramide compound having the formula (I):

$$R^1OOC\text{-}A\text{-}CONR^2R^3 \qquad (I)$$

in which:
$R^1$ is a radical selected from among saturated or unsaturated, linear or branched, optionally cyclic, optionally aromatic hydrocarbon-based radicals having an average number of carbon atoms ranging from 1 to 36;
$R^2$ and $R^3$, which may be identical or different, are each radicals selected from among saturated or unsaturated, linear or branched, optionally cyclic, optionally aromatic, optionally substituted hydrocarbon-based radicals having an average number of carbon atoms ranging from 1 to 36, with the proviso that $R^2$ and $R^3$ may optionally together form a ring member that is optionally substituted and/or that optionally contains a heteroatom; and
A is a branched divalent alkyl radical having an average number of carbon atoms ranging from 2 to 12,
(c) optionally at least one emulsifier; and
(d) optionally water;
wherein said active substance is solubilized in a solution comprising said at least one esteramide compound of formula (I).

26. The composition of claim 25, wherein said active substance is insoluble in water.

27. A method of solubilizing an active substance that is insoluble in water, said method comprising dissolving said active substance in at least one esteramide compound having the formula (I):

$$R^1OOC\text{-}A\text{-}CONR^2R^3 \qquad (I)$$

in which:
$R^1$ is a radical selected from among saturated or unsaturated, linear or branched, optionally cyclic, optionally aromatic hydrocarbon-based radicals having an average number of carbon atoms ranging from 1 to 36;
$R^2$ and $R^3$, which may be identical or different, are each radicals selected from among saturated or unsaturated, linear or branched, optionally cyclic, optionally aromatic, optionally substituted hydrocarbon-based radicals having an average number of carbon atoms ranging from 1 to 36, with the proviso that $R^2$ and $R^3$ may optionally together form a ring member that is optionally substituted and/or that optionally contains a heteroatom; and
A is a branched divalent alkyl radical having an average number of carbon atoms ranging from 2 to 12.

28. A composition comprising a mixture of two or more esteramide compounds having formula (I) below:

$$R^1OOC\text{-}A\text{-}CONR^2R^3 \qquad (I)$$

in which:
$R^1$ is a radical selected from among saturated or unsaturated, linear or branched, optionally cyclic, optionally aromatic hydrocarbon-based radicals having an average number of carbon atoms ranging from 1 to 36;
$R^2$ and $R^3$, which may be identical or different, are each radicals selected from among saturated or unsaturated, linear or branched, optionally cyclic, optionally aromatic, optionally substituted hydrocarbon-based radicals having an average number of carbon atoms ranging from 1 to 36, with the proviso that $R^2$ and $R^3$ may optionally together form a ring member that is optionally substituted and/or that optionally contains a heteroatom; and A is a branched divalent alkyl radical having an average number of carbon atoms ranging from 2 to 12.

29. The composition of claim 28, wherein said mixture of two or more esteramide compounds having formula (I) comprises:

$Me_2NOC—CH_2—CH(CH_2—CH_3)—COOMe$, $Me_2NOC—CH(CH_3)—CH_2—CH_2—COOMe$, and $Me_2NOC—CH_2—CH_2—CH(CH_3)—COOMe$.

* * * * *